United States Patent
De et al.

(10) Patent No.: US 6,545,038 B1
(45) Date of Patent: Apr. 8, 2003

(54) HETEROCYCLIC METALLOPROTEASE INHIBITORS

(75) Inventors: Biswanath De, Cincinnati, OH (US); Stanislaw Pikul, Mason, OH (US); Menyan Cheng, West Chester, OH (US); Neil Gregory Almstead, Loveland, OH (US); Randall Stryker Matthews, Cincinnati, OH (US); Michael George Natchus, Glendale, OH (US); Yetunde Olabisi Taiwo, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/707,212

(22) Filed: Nov. 6, 2000

Related U.S. Application Data

(62) Division of application No. 08/921,953, filed on Aug. 26, 1997, now Pat. No. 6,166,005.
(60) Provisional application No. 60/024,764, filed on Aug. 28, 1996.

(51) Int. Cl.[7] ............... A61K 31/675; A61K 31/38; A61K 31/335; C07D 267/00; C07D 281/00
(52) U.S. Cl. .................. 514/431; 514/79; 514/80; 514/450; 540/453; 540/454; 540/455; 540/456; 540/466; 540/467; 540/468
(58) Field of Search ............... 540/454, 466, 540/467, 453, 455, 456, 468; 514/431, 450, 79, 80

(56) References Cited

FOREIGN PATENT DOCUMENTS

WO   WO-98/08827 A1 * 3/1998

OTHER PUBLICATIONS

Almstead et al J. Med. Chem. 42 (1999) 4547–4562.*
Brown Expert Opin. Investig. Drugs 9(9) (2000) 2167–2177 (Medline abstract only).*
Heath et al Drugs 59(5) (2000) 1043–1055 (Medline abstract only).*
Scatena Expert Opin. Investig. Drugs 9(9) (2000) 2159–2165 (Medline abstract only).*
Shaw et al Expert Opin. Investig. Drugs 9(7) (2000) 1469–1478 (Medline abstract only).*
Steward et al Expert Opin. Investig. Drugs 9(12) (2000) 2913–2922 (Medline abstract only).*
Yip et al Invest. New Drugs 17(4) (1999) 387–399 (Medline abstract only).*
Katritzky et al., Heterocyclic Chemistry, John Wiley & Sons, Inc., 1960, pp. 247–253.*
Grant et al., Grant and Hackh's Chemical Dictionary, McGraw-Hill Book Company, 1987, p. 282.*
Borkakoti, N., Matrix Metalloproteases: Variations on a Theme, Progress in Biophysics & Molecular Biology, vol. 70, 1998, pp. 73–94.*
Yu et al., Matrix Metalloproteases: Novel Targets for Directed Cancer Therapy, Drugs & Aging, vol. 11, No. 3, 1997, pp. 229–244.*

* cited by examiner

*Primary Examiner*—Brenda Coleman
(74) *Attorney, Agent, or Firm*—David V. Upite; Carl J. Roof

(57) ABSTRACT

The invention provides compounds of formula (I)

as described in the claims, or an optical isomer, diastereomer or enantiomer thereof, or a pharmaceutically-acceptable salt, or biohydrolyzable amide, ester, or imide thereof are useful as inhibitors of metalloproteases.

Also disclosed are pharmaceutical compositions and methods of treating diseases, disorders and conditions characterized by metalloprotease activity using these compounds or the pharmaceutical compositions containing them.

15 Claims, No Drawings

HETEROCYCLIC METALLOPROTEASE INHIBITORS

CROSS REFERENCE TO RELATED APPLICATIONS

This is a divisional application of U.S. Ser. No. 08/921,953, now U.S. Pat. No. 6,166,005 which was filed Aug. 26, 1997 and claims priority to provisional application U.S. Ser. No. 60/024,764, filed Aug. 28, 1996.

TECHNICAL FIELD

This invention is directed to compounds which are useful in treating diseases, disorders and conditions associated with unwanted metalloprotease activity.

BACKGROUND

A number of structurally related metalloproteases [MPs] effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 *J. Cell Bio.* 275–78 October, 1995), and the enkephalinases. Examples of MPs include human skin fibroblast collagenase, human skin fibroblast gelatinase, human sputum collagenase, aggrecanse and gelatinase, and human stromelysin. Collagenase, collagenase, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5.403,952 (Merck & Co.); PCT published application WO 96/06074 (British Bio Tech Ltd); PCT Publication WO 96/00214 (Ciba Geigy); WO 95/35275 (British: Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd); WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/9965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 (Merck); WO 94/0019 (Glaxo); WO 93/21942 (British Bio Tech Ltd), WO 92/22523 (Res. Corp. Tech. Inc.); WO 94/10990 (British Bio (Yamanouchi): and British patents GB 2282598 (Merck) and GB 2268934 (British Bio Tech Ltd); Published European Patent Applications EP 95/684240 (Hoffman LaRoche); EP 574758 (Hoffman LaRoche): EP 575844 (Hoffman LaRoche) Published Japanese applications; JP 08053403 (Fujusowa Pharm. Co: Ltd.); JP 7304770 (Kanebo Ltd.); and Bird et all *J. Med Chem* vol. 37, pp. 158–69 (1994). Examples of potential therapeutic uses of MP inhibitors include rheumatoid arthritis (Mullins, D. E. et al., *Biochim. Biophys. Acta.* (1983) 695:117–214); osteoarthritis (Henderson, B. et al., *Drugs of the Future* (1990) 15:495–508); the metastasis of tumor cells (ibid, Broadhurst, M. J., et al., European Patent Application 276,436 (published 1987), Reich, R., et al. 48 *Cancer Res.* 3307–3312 (1988); and various ulcerations or ulcerative conditions of tissue. For example, ulcerative conditions can result in the cornea as the result of alkali burns or as a result of infection by Pseudomonas aeruginosa, Acanthamoeba, Herpes simplex and vaccinia viruses.

Other examples of conditions characterized by undesired metalloprotease activity include periodontal disease, epidermolysis bullosa, fever, inflammation and scleritis (Cf. DeCicco et al, WO 95 29892 published November 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

Metalloprotease inhibitors are useful in treating diseases caused, at least in part, by breakdown of structural proteins. Though a variety of inhibitors have been prepared, there is a continuing need for potent matrix metalloprotease inhibitors useful in treating such diseases. Applicants have found that, surprisingly, the compounds of the present invention are potent metalloprotease inhibitors.

OBJECTS OF THE INVENTION

Thus it is an object of the present invention to provide compounds useful for the treatment of conditions and diseases which are characterized by unwanted MP activity.

It is also an object of the invention to provide potent inhibitors of metalloproteases.

It is a further object of the invention to provide pharmaceutical compositions comprising such inhibitors.

It is also an object of the invention to provide a method of treatment for metalloprotease related maladies.

SUMMARY OF THE INVENTION

The invention provides compounds which are useful as inhibitors of metalloproteases, and which are effective in treating conditions characterized by excess activity of these enzymes. In particular, the present invention relates to a compound having a structure according to Formula (I)

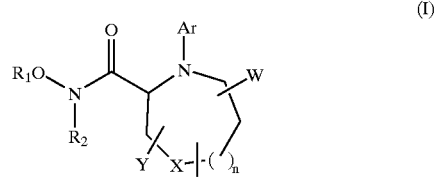

wherein $R_1$ is H;

$R_2$ is hydrogen, alkyl or acyl;

Ar is $COR_3$ or $SO_2R_4$; and $R_3$ is alkoxy, aryloxy, heteroaryloxy, alkyl, aryl, heteroaryl, heteroalkyl, amino, alkylamino, dialkylamino, arylamino and alkylarylamino;

$R_4$ is alkyl, heteroalkyl, aryl, or heteroaryl, substituted or unsubstituted;

Ar is substituted phenyl, the substituents are hydroxy, alkoxy, nitro or halo and preferably the substituents are methoxy, bromo, nitro and butoxy.

X is $CH_2$, O, S, SO, $SO_2$, or $NR_5$, wherein $R_5$ is independently chosen from hydrogen, alkyl, heteroalkyl, heteroaryl, aryl, $SO_2R_6$, $COR_7$, $CSR_8$, $PO(R_9)_2$ or may optionally form a ring with W; and $R_6$ is alkyl, aryl, heteroaryl, heteroalkyl, amino, alkylamino, dialkylamino, arylamino, diarylamino and alkylarylamino;

$R_7$ is hydrogen, alkoxy, aryloxy, heteroaryloxy, alkyl, aryl, heteroaryl, heteroalkyl, amino, alkylamino, dialkylamino, arylamino and alkylarylamino;

$R_8$ is alkyl, aryl, heteroaryl, heteroalkyl, amino, alkylamino, dialkylamino, arylamino, diarylamino and alkylarylamino;

$R_9$ is alkyl, aryl, heteroaryl, heteroalkyl;

W is hydrogen or one or more lower alkyl moieties, or is an alkylene, arylene, or heteroarylene bridge between two adjacent or nonadjacent carbons (thus forming a fused ring);

Y is independently one or more of hydrogen, hydroxy, $SR_{10}$, $SOR_4$, $SO_2R_4$, alkoxy, amino, wherein amino is of formula $NR_{11}R_{12}$, wherein $R_{11}$ and $R_{12}$ are independently chosen from hydrogen, alkyl, heteroalkyl, heteroaryl, aryl, $SO_2R_6$, $COR_7$, $CSR_8$, $PO(R_9)_2$; and $R_{10}$ is hydrogen, alkyl, aryl, heteroaryl;

Z is nil, a spiro moiety or an oxo group substituted on the heterocyclic ring;

n is 1–3.

This structure also includes an optical isomer, diastereomer or enantiomer for Formula (I). or a pharmaceutically-acceptable salt, or biohydrolyzable amide, ester, or imide thereof.

These compounds have the ability to inhibit at least one mammalian metalloprotease. Accordingly, in other aspects, the invention is directed to pharmaceutical compositions containing the compounds of Formula (I), and to methods of treating diseases characterized by unwanted metalloprotease activity using these compounds or the pharmaceutical compositions containing them.

Metalloproteases which are active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease, preferably a matrix metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

DETAILED DESCRIPTION

The compounds of the present invention are inhibitors of mammalian metalloproteases, preferably a matrix metalloproteases. Preferably, the compounds are those of Formula (I) or a pharmaceutically-acceptable salt, or biohydrolyzable amide, ester, or imide thereof.

Throughout this disclosure, publications and patents are referred to in an effort to fully describe the state of the art. All references cited herein are hereby incorporated by reference.

Definitions and Usage of Terms

The following is a list of definitions for terms used herein.

"Acyl" or "carbonyl" is described as a radical which could be formed by removal of the hydroxy from a carboxylic acid (i.e., R—C(=O)—). Preferred acyl groups include (for example) acetyl, formyl, and propionyl.

"Acyloxy" is an oxy radical having an acyl substituent (i.e., —O-acyl); for example, —O—C(=O)-alkyl.

"Alkoxyacyl" is an acyl radical (—C(=O)—) having an alkoxy substituent (i.e., —O—R), for example, —C(=O)—O-alkyl. This radical can be referred to as an ester.

"Acylamino" is an amino radical having an acyl substituent (i.e. —N-acyl); for example. —NH—C(=O)-alkyl.

"Alkenyl" is an unsubstituted or substituted hydrocarbon chain radical having 2 to 15 carbon atoms: preferably from 2 to 10 carbon atoms; more preferably from 2 to 8; except where indicated. Alkenyl substituents have at least one olefinic double bond (including, for example. vinyl, allyl and butenyl).

"Alkynyl" is an unsubstituted or substituted hydrocarbon chain radical having 2 to 15 carbon atoms; preferably from 2 to 10 carbon atoms; more preferably from 2 to 8; except where indicated. The chain has at least one carbon-carbon triple bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., -alkyl-O-alkyl). Preferred is where the alkyl has 1 to 6 carbon atoms (more preferably 1 to 3 carbon atoms), and the alkyoxy has 1 to 6 carbon atoms (more preferably 1 to 3 carbon atoms).

"Alkyl" is an unsubstituted or substituted saturated hydrocarbon chain radical having 1 to 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

As referred to herein, "spiro cycle" or "spiro cyclic" refers to a cyclic moiety sharing a carbon on another ring. Such cyclic moiety may be carbocyclic or heterocyclic in nature. Preferred heteroatoms included in the backbone of the heterocyclic spirocycle include oxygen, nitrogen and sulfur. The spiro cycles may be unsubstituted or substituted. Preferred substituents include oxo, hydroxy, alkyl, cycloalkyl, arylalkyl, alkoxy, amino, heteroalkyl, aryloxy, fused rings (e.g., benzothiole, cycloalkyl, heterocycloalkyl, benzimidizoles, pyridylthiole, etc., which may also be substituted) and the like. In addition, the heteroatom of the heterocycle may be substituted if valence allows. Preferred spirocyclic ring sizes include 3–7 membered rings.

Alkylene refers to an alkyl, alkenyl or alkynyl which is diradical, rather than a radical. "Hetero alkylene" is likewise defined as a (diradical) alkylene having a heteroatom in its chain.

"Alkylamino" is an amino radical having one (secondary amine) or two (tertiary amine) alkyl substituents (i.e., —N-alkyl). For example, methylamino (—NHCH$_3$), dimethylamino (—N(CH$_3$)$_2$), methylethylamino (—N(CH$_3$)CH$_2$CH$_3$).

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl, naphthyl, biphenyl and fluorenyl. Such groups may be substituted or unsubstituted.

"Arylalkyl" is an alkyl radical substituted with an aryl group. Preferred arylalkyl groups include benzyl, phenylethyl, and phenylpropyl. Such groups may be substituted or unsubstituted. "Arylalkylamino" is an amine radical substituted with an arylalkyl group (e.g., —NH-benzyl). Such groups may be substituted or unsubstituted.

"Arylamino" is an amine radical substituted with an aryl group (i.e., —NH-aryl). Such groups may be substituted or unsubstituted.

"Aryloxy" is an oxygen radical having an aryl substituent (i.e., —O-aryl). Such groups may be substituted or unsubstituted.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 4 to 9 atoms, preferably 4 to 7 atoms. Polycyclic carbocyclic rings contain 7 to 17 atoms, preferably from 7 to 12 atoms. Preferred polycyclic systems comprise 4-, 5-, 6- or 7-membered rings fused to 5-, 6-, or 7-membered rings.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with a carboxy (—C(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholinyl, piperadinyl, piperazinyl, tetrahydrofuryl and hydantoinyl.

"Fused rings" are rings that are superimposed together such that they share two ring atoms. A given ring may be fused to more than one other ring. Fused rings are contemplated in heteroaryl, aryl and heterocycle radicals or the like.

"Heterocycle-alkyl" is an alkyl radical substituted with a heterocyclic ring. The heterocyclic ring is preferably a heteroaryl or cycloheteroalkyl, more preferably a heteroaryl. Preferred heterocycle alkyl include C$_1$–C$_4$ alkyl having preferred heteroaryl appended to them. More preferred is, for example, pyridyl alkyl and the like.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3 to 8 members comprising carbon atoms and one or two heteroatoms. The chain has at least one carbon-carbon double bond.

"Heteroalkyl" is an unsubstituted or substituted saturated chain radical having 2 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or Spiro polycyclic ring systems. Monocyclic heterocyclic rings contain 3 to 9 atoms, preferably 4 to 7 atoms. Polycyclic rings contain 7 to 17 atoms, preferably from 7 to 13 atoms.

"Heteroaryl" is an aromatic heterocyclic ring, either monocyclic or bicyclic radical. Preferred heteroaryl groups include (for example) thienyl, furyl, pyrrolyl, pyridinyl, pyrazinyl, thiazolyl, pyrimidinyl, quinolinyl, and tetrazolyl, benzo thiazolyl, benzofuryl, indolyl and the like. Such groups may be substituted or unsubstituted.

"Halo", "halogen", Or "halide" is a chloro, bromo, fluoro or iodo atom radical. Bromo, chloro and fluoro are preferred halides.

Also, as referred to herein, a "lower" hydrocarbon moiety (c.g., "lower" alkyl) is a hydrocarbon chain comprised of 1 to 6, preferably from 1 to 4, carbon atoms.

A "pharmaceutically-acceptable salt" is a cationic salt formed at any acidic (e.g., carboxyl) group, or an anionic salt, formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium) and organic salts. Preferred anionic salts include the halides (such as chloride salts).

"Biohydrolyzable amides" are amides of the compounds of the invention that do not interfere with the inhibitory activity of the compound, or that arc readily converted in vivo by a mammal subject to yield an active inhibitor.

A "biohydrolyzable hydroxy imide" is an imide of a Formula (I) compound that does not interfere with the metalloprotease inhibitory activity of these compounds, or that is readily converted in vivo by a mammal subject to yield an active Formula (I) compound. Such hydroxy imides include those that do not interfere with the biological activity of the Formula (I) compounds.

A "biohydrolyzable ester" refers to an ester of a Formula (I) compound that does not interfere with the metalloprotease inhibitory activity of these compounds or that is readily converted by an animal to yield an active Formula (I) compound.

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

"Optical isomer", "stereoisomer", "diastereomer" as referred to herein have the standard art recognized meanings (Cf., *Hawley's Condensed Chemical Dictionary*, 11th Ed.).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammnalian metalloprotease" means any metal-containing enzyme found in mammalian sources which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345, use of a synthetic substrate is described by Weingarten, H., et al., *Biochem. Biophy. Res. Comm.* (1984) 139:1184–1187. Any standard method for analyzing the breakdown of these structural proteins can, of course, be used. The metalloprotease enzymes referred to herein are all zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds. or crude extracts which contain the range of enzymes capable of tissue breakdown can be used.

Compounds

Compounds of the invention are described in the Summary of the Invention. Preferred compounds of the invention are those in which Z is heterospiroalkylene, preferably having heteroatoms adjacent to the parent ring structure, more preferably such spiroheteroalkylenes have 4 to 5 members. Preferred heteroatoms are divalent.

The invention provides compounds which are useful as inhibitors of metalloproteases, preferably a matrix metalloproteases, and which are effective in treating conditions characterized by excess activity of these enzymes. In particular, the present invention relates to a compound having a structure according to Formula (I)

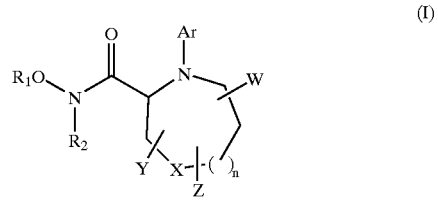

wherein $R_1$ is H;

$R_2$ is hydrogen, alkyl or acyl;

Ar is $COR_3$ or $SO_2R_4$; and $R_3$ is alkoxy, aryloxy, heteroaryloxy, alkyl, aryl, heteroaryl, heteroalkyl, amino, alkylamino, dialkylamino, arylamino and alkylarylamino;

$R_4$ is alkyl, heteroalkyl, aryl, or heteroaryl, substituted or unsubstituted;

X is $CH_2$, O, S, SO, $SO_2$, or $NR_5$, wherein $R_5$ is independently chosen from hydrogen, alkyl, heteroalkyl, heteroaryl, aryl, $SO_2R_6$, $COR_7$, $CSR_8$, $PO(R_9)_2$ or may optionally form a ring with W; and $R_6$ is alkyl, aryl, heteroaryl, heteroalkyl, amino, alkylamino, dialkylamino, arylamino, diarylamino and alkylarylamino;

$R_7$ is hydrogen, alkoxy, aryloxy, heteroaryloxy, alkyl, aryl, heteroaryl, heteroalkyl, amino, alkylamino, dialkylamino, arylamino and alkylarylamino;

$R_8$ is alkyl, aryl, heteroaryl, heteroalkyl, amino, alkylamino, dialkylamino, arylamino, diarylamino and alkylarylamino;

$R_9$ is alkyl, aryl, heteroaryl, heteroalkyl;

W is hydrogen or one or more lower alkyl moieties, or is an alkylene, arylene, or heteroarylene bridge between two adjacent or nonadjacent carbons (thus forming a fused ring);

Y is independently one or more of hydrogen, hydroxy, $SR_{10}$, $SOR_4$, $SO_2R_4$, alkoxy, amino, wherein amino is of formula $NR_{11}R_{12}$, wherein $R_{11}$ and $R_{12}$ are independently chosen from hydrogen, alkyl, heteroalkyl, heteroaryl, aryl, $SO_2R_6$, $COR_7$, $CSR_8$, $PO(R_9)_2$, and $R_{10}$ is hydrogen, alkyl, aryl, heteroaryl;

Z is nil, a spiro moiety or an oxo group substituted on the heterocyclic ring;

n is 1–3.

This structure also includes an optical isomer, diastereomer or enantiomer for Formula (I), or a pharmaceutically-acceptable salt, or biohydrolyzable ester, amide, or imide thereof.

Compound Preparation

The hydroxamic compounds of Formula (I) can be prepared using a variety of procedures. General schemes include the following.

PREPARATION OF THE Y MOIETY

For the manipulation of Y it is understood that the skilled artisan may choose to prepare Y before, after or concurrent with the preparation of the heterocyclic ring. For clarity, the W and Z moiety are not shown below. More than one Y and Z may be present in the compounds of formula (I). For compounds where Y is not adjacent to the ring nitrogen, a preferred method of making the compounds is;

SCHEME I

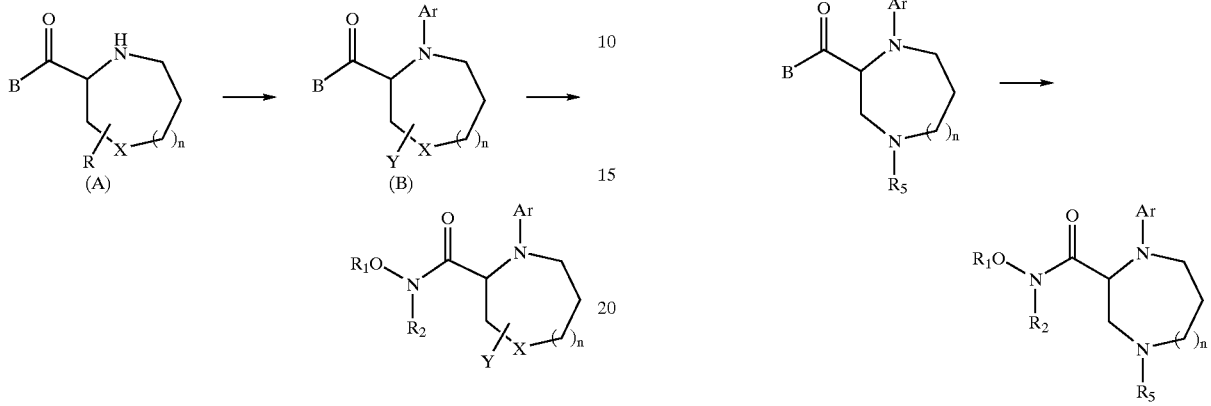

Where R is a derivatizable group or can be manipulated or substituted, such compounds are known or are prepared by known methods. (A) is converted to its analogous sultamester and R is manipulated to give (B) during this or a subsequent step. Y and Z can be added or altered, followed by appropriate reaction to provide $R_1$. For example, this step may include treatment with hydroxyl amine under basic conditions to give a compound of formula I (C).

For the preparation and elaboration of the heterocyclic ring it is understood that the skilled artisan may choose to prepare Y before, after or concurrent with the preparation of the heterocyclic ring. For clarity, the W, Y, and Z moiety are not shown below. More than one W, Y and Z may be present in the compounds of formula (I). For compounds where X is nitrogen, the preferred method for the manipulation of $R_5$ is shown. In the scheme below, L is any acceptable leaving group, and B is a blocking group as above, Boc is an example of a preferred, and art recognized blocking group. The skilled artisan will recognize that the choice of blocking group is within the skill of the artisan working in organic chemistry. Thus the choice of Boc is not required, but preferred.

SCHEME II

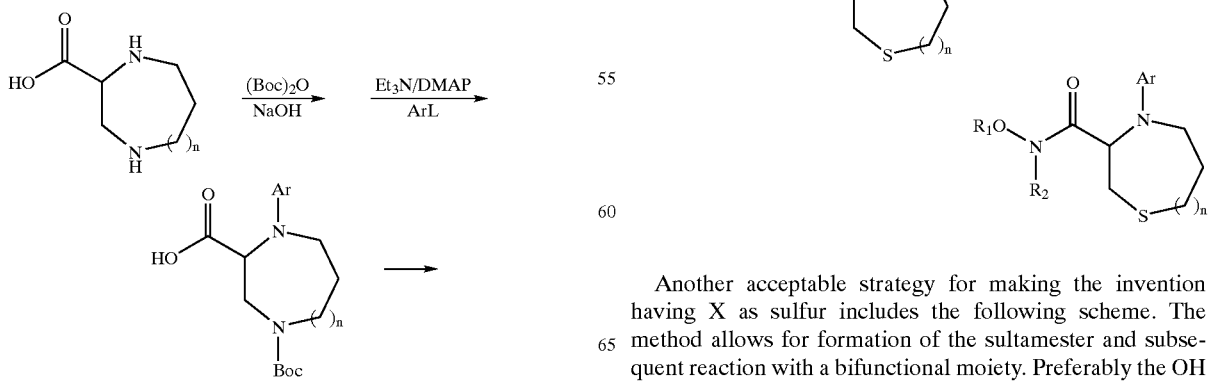

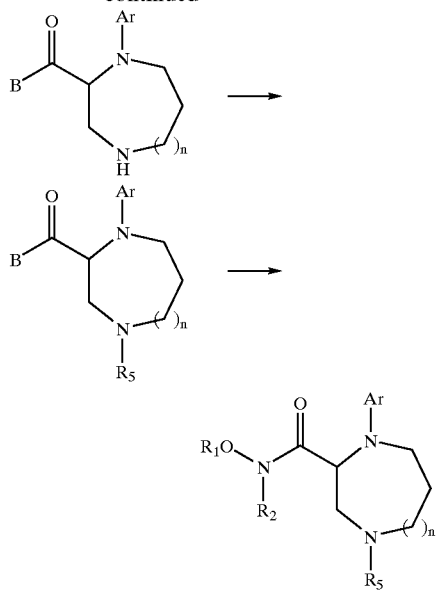

For compounds containing a sulfur in the heterocyclic ring the preferred methods of ring formation are shown. For the preparation and elaboration of the heterocyclic ring it is understood that the skilled artisan may choose to prepare Y before, after or concurrent with the preparation of the heterocyclic ring. For clarity, the W, Y, and Z moiety are not shown below. More than one W, Y and Z may be present in the compounds of formula (I).

SCHEME III

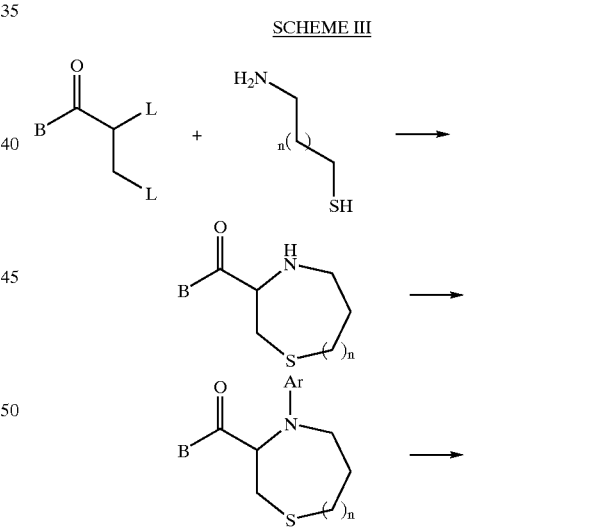

Another acceptable strategy for making the invention having X as sulfur includes the following scheme. The method allows for formation of the sultamester and subsequent reaction with a bifunctional moiety. Preferably the OH described in the scheme below is a primary hydroxyl.

Closure of the ring uses standard methods. Functionalization and elaboration of the molecule proceeds as described above.

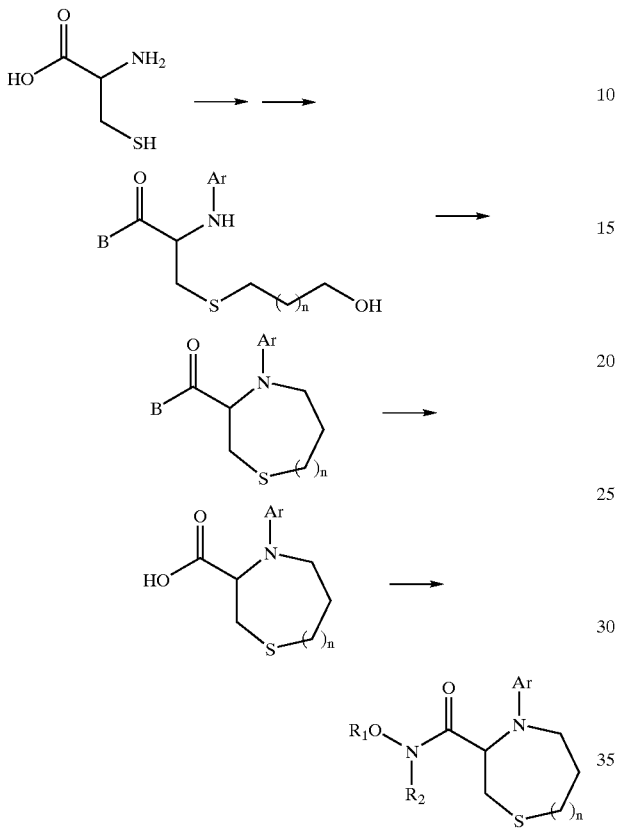

Where X is sulfur, further elaboration of the heterocyclic ring can be accomplished after the ring has been formed. For example, oxidation of the ring sulfur atom using known methods can provide the corresponding sulfoxides and sulfones as shown.

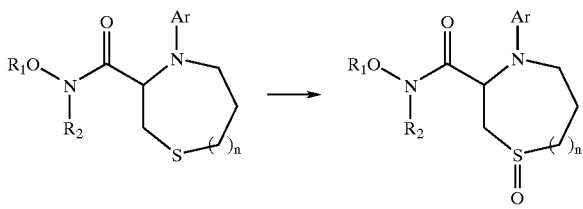

For compounds containing an oxygen in the heterocyclic ring the preferred methods of ring formation are shown. A bifunctional moiety, for example a halo hydroxy species is reacted with an aziridine as shown below. The halo moiety serves as a leaving group, useful in the ring closure reactions. Upon formation of the ring, elaboration of the invention proceeds as described above.

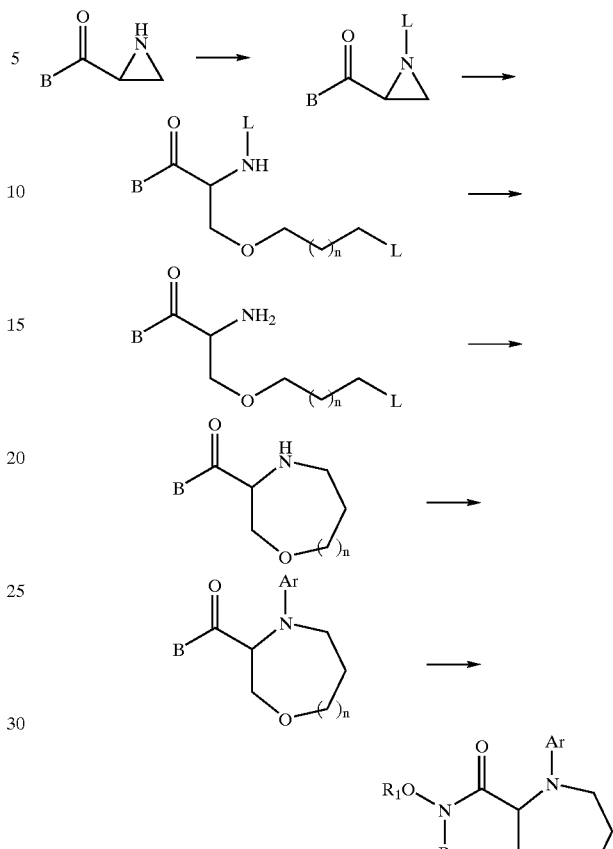

PREPARATION OF THE Z MOIETY

Of course the skilled artisan will recognize that schemes applicable to the preparation of Y may be useful in the preparation of Z as noted above. Other preferred methods are provided for the reader.

Where Z is a ketal or thioketal the compounds of the invention may be prepared from a compound having a carbonyl in the ring. Such compounds are prepared by known methods, and many of such compounds are known or commercially available. Thus the skilled artisan will appreciate that a hydroxy, amino, imino, alkoxy, oxo or any other group that may be manipulated into a carbonyl compound. The order of elaborating the ketal, $R_1$ or the sultamester may be changed.

A preferred method of making the spiro compounds of the invention is via a carbonyl compound, using "protecting group" technology known in the art, such as a thioketal or ketal, and the like. Ketals, acetals and the like are prepared from carbonyl compounds by methods known in the art. Such carbonyl compounds can be made of cyclic hydroxy alkylene amines via oxidation to a ketone, or of lactams, which provide for 2-amino spiro functionality.

A variety of compounds can be generated in a similar fashion, using the guidance of the scheme above.

In the above schemes, where R' is alkoxy or alkylthio, the corresponding hydroxy or thiol compounds are derived from the final compounds by using a standard dealkylating procedure (Bhatt, et al. "Cleavage of Ethers", *Synthesis*, 1983, pp. 249–281).

These steps may be varied to increase yield of desired product. The skilled artisan will also recognize the judicious choice of reactants, solvents, and temperatures is an important component in successful synthesis. While the determination of optimal conditions, etc. is routine, it will be understood that to make a variety of compounds can be generated in a similar fashion, using the guidance of the scheme above.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and Keeting, *Heterocyclic Chemistry* (all 17 volumes).

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of Use

Metalloproteases (MPs) found in the body operate, in part, by breaking down the extracellular matrix, which comprises extracellular proteins and glycoproteins. These proteins and glycoproteins play an important role in maintaining the size, shape, structure and stability of tissue in the body. Inhibitors of metalloproteases are useful in treating diseases caused, at least in part, by breakdown of such proteins. It is known that MPs are intimately involved in tissue remodeling. As a result of this activity they have been said to be active in many disorders involving either the:

breakdown of tissues; including degenerative diseases, such as arthritis, multiple sclerosis and the like; metastasis or mobility of tissues in the body:

the remodeling of tissues, including fibrotic disease, scarring, benign hyperplasia, and the like.

The compounds of the present invention treat disorders, diseases and/or unwanted conditions which are characterized by unwanted or elevated activity by that class of proteases. For example the compounds can be used to inhibit proteases which destroy structural proteins (i.e. the proteins that maintain tissue stability and structure);

interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561], and/or facilitate processes which are undesired in the subject being treated, for example, the processes of sperm maturation, egg fertilization and the like.

As used herein, a "MP related disorder" or "a MP related disease" is one that involves unwanted or elevated MP activity in the biological manifestation of the disease or disorder; in the biological cascade leading to the disorder; or as a symptom of the disorder. This "involvement" of the MP includes;

The unwanted or elevated MP activity as a "cause" of the disorder or biological manifestation, whether the activity was elevated genetically, by infection, by autoimmunity, trauma, biomechanical causes, lifestyle [e.g. obesity] or by some other cause;

The MP as part of the observable manifestation of the disease or disorder. That is, the disease or disorder is measurable in terms of the increased MP activity, or from a clinical standpoint. unwanted or elevated MP levels indicate the disease. MPs need not be the "hallmark" of the disease or disorder;

The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus the distribution of MPs expressed in various tissues are often specific to those tissues. For example, the distribution of metalloproteases implicated in the breakdown of tissues in the joints, is not the same as the distribution of metalloproteases found in other tissues Thus, though not essential for activity or efficacy, certain disorders preferably are treated with compounds that act on specific MPs found in the affected tissues or regions of the body. For example, a compound which displays a higher degree of affinity and inhibition for a MP found in the joints (e.g. chondrocytes) would be preferred for treatment of disease found there than other compounds which are less specific.

In addition, certain inhibitors are more bioavailable to certain tissues than others, and this judicious choice of inhibitor, with the selectivity described above provides for specific treatment of the disorder, disease or unwanted condition. For example, compounds of this invention vary in their ability to penetrate into the central nervous system.

Thus compounds may be selected to produce effects mediated through MPs found specifically outside the central nervous system.

Determination of the specificity of a MP inhibitor of a certain MP is within the skill of the is artisan in that field. Appropriate assay conditions can be found in the literature. Specifically assays are known for stromelysin and collagenase. For example, U.S. Pat. No. 4,743,587 references the procedure of Cawston, et al., *Anal Biochem* (1979) 99:340–345. The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

As a result of the MP inhibitory effect of the compounds of the invention, the compounds of the invention are also useful in treating the following disorders by virtue of their metalloprotease activity.

The compounds of this invention are also useful for the prophylactic or acute treatment. They are administered in any way the skilled artisan in the fields of medicine or pharmacology would desire. It is immediately apparent to the skilled artisan that preferred routes of administration will depend upon the disease state being treated, and the dosage form chosen. Preferred routes for systemic administration include administration perorally or parenterally.

However, the skilled artisan will readily appreciate the advantage of administering the MP inhibitor directly to the affected area for many disorders. For example, it may be advantageous to administer MP inhibitors directly to the area of the disease or condition as in area affected by surgical trauma (e.g., angioplasty), area affected by scarring or burn (e.g., topical to the skin), Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure overtime) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet, damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MIPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; [CMV] retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response, and in the processing of cytokine the compounds are also useful as anti-inflammatories, for use in disease where inflammation is prevalent including, inflammatory bowel disease. Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially comeal ulceration, lack of corneal healing, macular degeneration, and pterygium), and gum, disease (especially periodontal disease, and gingivitis)

Compounds preferred for, but not limited to, the treatment of arthritis (including osteoarthritis and rheumatoid arthritis) are those compounds that are selective for the metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions

The compositions of the invention comprise:
(a) a safe and effective amount of a compound of Formula (I); and
(b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to inhibit metalloproteases at the site(s) of activity, in a mammal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the aminal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers, antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to a aminal, preferably mammal subject, in a single dose, according to good medical practice. These compositions preferably contain from about 5 mg (milligrams) to about 1000 mg, more preferably from about 10 mg to 30 about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors. 1979); Lieberman et al., *Pharmaceutical Dosage Forms: Tablets* (1981); and Ansel. *Introduction to Pharmaceutical Dosage Forms* 2d Edition (1976).

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a aminal, preferably mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the aminal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, solvents and the like.

Methods of Administration

This invention also provides methods of treating or preventing disorders associated with excess or undesired metalloprotease activity in an animal, preferably mammal subject, by administering a safe and effective amount of a Formula (I) compound to said subject. As used herein, a "disorder associated with excess or undesired metalloprotease activity" is any disorder characterized by degradation of proteins. The methods of the invention are useful in treating disorders such as (for example) osteoarthritis, periodontitis, corneal ulceration, tumor invasion, and rheumatoid arthritis.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serun. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassay.

The following non-limiting examples illustrate the compounds, compositions, and uses of the present invention.

EXAMPLES

Compounds are analyzed using $^1$H and $^{13}$C NMR. Elemental analysis, mass spectra and/or IR spectra, as appropriate.

Typically inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh: Aldrich) or (230–400 mesh; Merck) as appropriate. Thin layer chromatography analysis (TLC) is performed on glass mounted silica gel plates (200–300 mesh; Baker) and visualized with UV or 5% phosphomolybdic acid in EtOH.

Example 1

Preparation of N-Hydroxy-2,2dimethyl-S,S-dioxo-4-[(4-methoxyphenyl)sulfonyl]thiazepine-3(S)-carboxamide

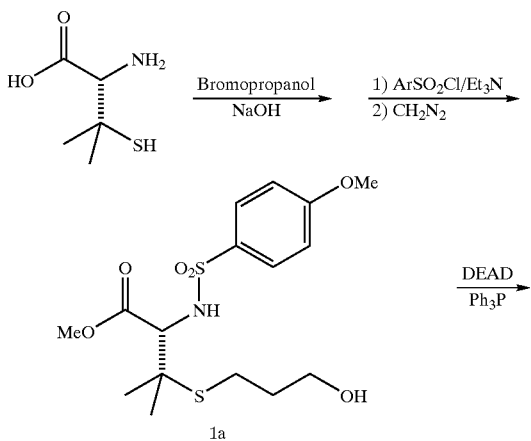

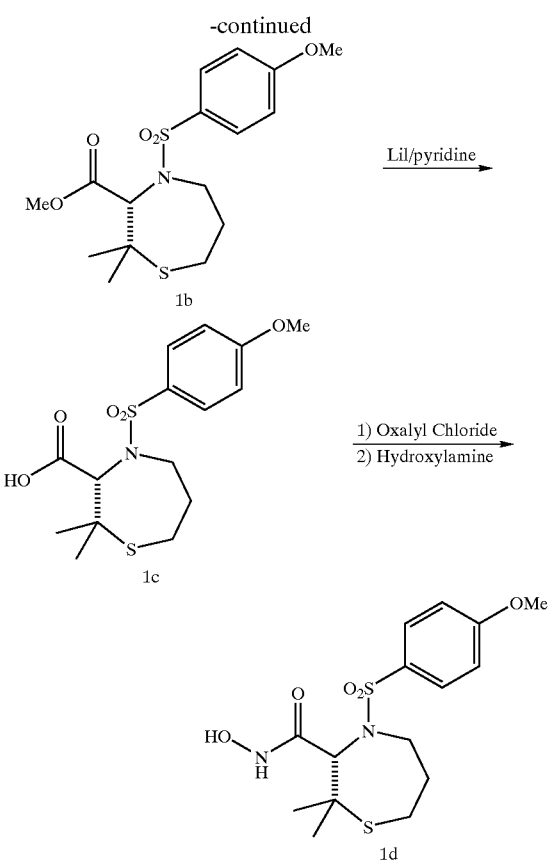

1a. Methyl N-[(4methoxyphenyl)sulfonyl]-S(2-hydroxypropyl)-D-penicillamine: D-Penicillamine (29.8 g, 0.2 mol) in 2N NaOH (135 mL, 0.27 mol, 1.35 equiv) is stirred at 0° C. under an Argon atmosphere. A solution of 2-bromopropanol (36.1 g, 0.26 mol, 1.3 equiv) in ethanol (200 mL) is slowly added dropwise at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (200 mL) and water (200 mL) and stirred at room temperature. Triethylamine (58.6 g, 0.58 mol, 3 equiv) is then added to the reaction mixture followed by 4-methoxyphenylsulfonyl chloride (40.0 g, 0.193 mol). The resulting homogeneous solution is stirred at room temperature for 18 hours and then acidified to pH ~2 with 1N HCl. The solution is poured into water and extracted with methylene chloride. The organic extracts were dried (MgSO$_4$) and concentrated to an oil under reduced pressure. The resulting oil is diluted in methanol (30 mL) and enough diazomethane in diethyl ether is added to form a yellow solution. The mixture is concentrated under reduced pressure to leave a colorless oil. Purification of the resulting methyl ester is accomplished by chromatography on silica gel using 1/1 hexane/EtOAc as the eluent. The desired product is obtained as a clear, colorless oil.

1b. Methyl 4N-[(4-methoxyphenyl)sulfonyl]-2,2-dimethyl-thiazepine-3-carboxylate: The methyl ester 1a (30.0 g. 76.6 mmol) in THF (400 mL) is stirred at room temperature and then triphenylphosphine (24.1 g. 91.9 mmol. 1.2 equiv) followed by diethyl azodicarboxylate (14.7 g, 84.3 mmol. 1.1 equiv) is added. The resulting solution is stirred at room temperature for 2 hours. The solvent is removed and then the thick yellow oil is diluted with methylene chloride and silica gel (60 g) is added. The solvent is removed to leave a white powder. This powder is placed upon a chromatography column and eluted with 8/2 hexane,EtOAc. The desired product is obtained as a colorless oil. MS (ESI): 374 (M$^+$+H), 391 (M$^+$+NH$_4$).

1c. 4-[(4-methoxyphenyl)sulfonyl]-2,2-dimethyl-thiazepine-3-carboxylic acid: The methyl ester 1b (26.7 g, 71.5 mmol) in pyridine (400 mL) is stirred at room temperature under an argon atmosphere. Lithium iodide (115 g, 858 mmol, 12 equiv) is added and the resulting solution is heated to reflux for 3 h. The reaction mixture is cooled to room temperature and then the solution is acidified with 1N HCl. The mixture is extracted with methylene chloride and then the organic extracts were dried (Na$_2$SO$_4$) and concentrated to an oil under reduced pressure. The oil is purified by column chromatography using 1/1 hexane/EtOAc as the eluent to provide the desired product as a light yellow oil. MS (ESI): 360 (M$^+$+H), 377 (M$^+$+NH$_4$).

1d. N-Hydroxy-4-[(4-methoxyphenyl)sulfonyl]-2,2-dimethyl-thiazepine-3-carboxamide: The carboxylic acid 1c (14.9 g, 41.6 mmol) in dichloromethane (200 mL) is stirred at room temperature and then oxalyl chloride (10.8 g, 85.2 mmol, 2.05 equiv) and DMF (3.04 g, 41.6 mmol) are added. The resulting solution is stirred at room temperature for 30 minutes. In a separate flask, hydroxylamine hydrochloride (11.6 g, 166 mmol, 4 equiv) in THF (50 mL) and water (10 mL) is stirred at 0° C. Triethylamine (25.3 g, 249.6 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts were dried (Na$_2$SO$_4$) and concentrated to a solid under reduced pressure. The solid is recrystallized from CH$_3$CN to provide a white powder. MS (ESI): 392 (M$^+$+NH$_4$), 375 (M$^+$+H).

Example 2

Preparation of N-Hydroxy-S,S-dioxo-4-[(4-methoxyphenyl)sulfonyl]-2,2-dimethyl-thiazepine-3-carboxamide

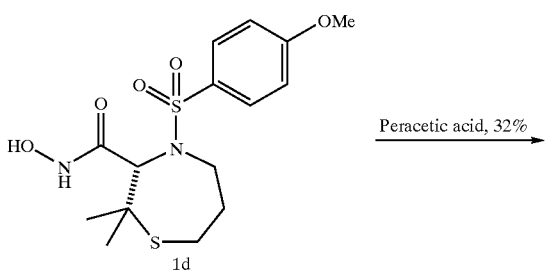

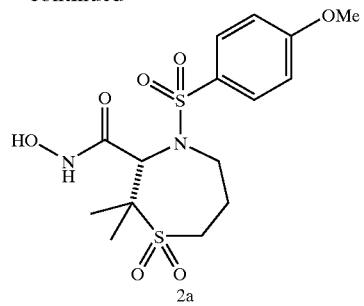

2a. N-Hydroxy-S,S-dioxo-4-[(4-methoxyphenyl)sulfonyl]-2,2-dimethyl-thiazepine-3-carboxamide: The hydroxamic acid 1d (4.7 g, 12.55 mmol) is dissolved in chloroform (50 mL) at 0° C. in an ice bath. A solution of 32% peracetic acid (7.9 mL, 37.65 mmol, 3.0 equiv in acetic acid) is added and the mixture is then stirred at room temperature. An additional 3 equiv of 32% peracetic acid is added after 3 hours and the resulting mixture is stirred overnight. Once the reaction is complete, the peracetic acid is removed under reduced pressure. The white solid is recrystallized with acetonitrile to provide a white powder. MS (ESI): 407 (M$^+$+H).

Example 3

Preparation of 3(S)-N-Hydroxy-N-methyl-2,2-dimethyl-4N-[(4-methoxyphenyl)sulfonyl]-thiazepine-3-carboxamide

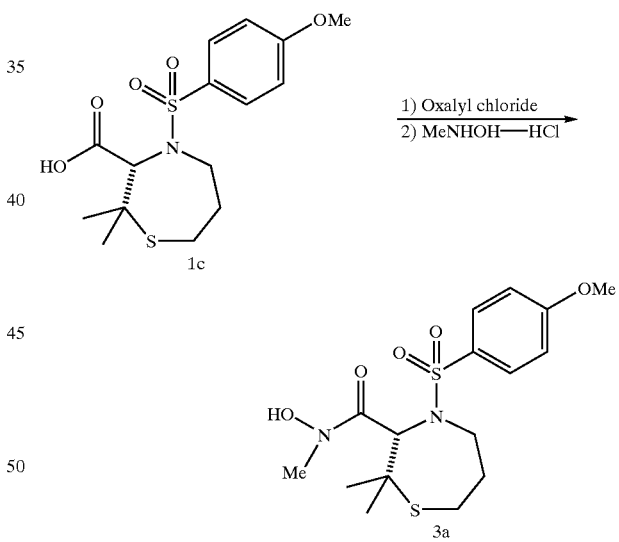

3a. 3(S)-N-Hydroxy-N-methyl-2,2-dimethyl-4N-[(4-methoxyphenyl)sulfonyl]-thiazepine-3-carboxamide: The carboxylic acid 1c (1.10 g, 3.06 mmol) in dichloromethane (25 mL) is stirred at room temperature and then oxalyl chloride (0.80 g,6.27 mmol, 2.05 equiv) and DMF (0.22 g, 3.06 mmol) are added. The resulting solution is stirred at room temperature for 30 minutes. In a separate flask, N-methylhydroxylamine hydrochloride (1.02 g, 12.24 mmol, 4 equiv) in THF (8 mL) and water (2 mL) are stirred at 0° C. Triethylamine (1.85 g, 18.4 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is acidified with 1 N HCl and then extracted with dichloromethane. The organic extracts are dried (Na$_2$SO$_4$) and concentrated to a solid under reduced pressure. The solid is purified by reverse phase (C$_{18}$) HPLC chromatography to provide a white powder. MS (ESI): 389 (M$^+$+H).

Example 4

Preparation of N-Hydroxy-S,S-dioxo-2,2-dimethyl-4-[(4-bromophenyl)sulfonyl]thiazepine-3(S)-carboxamide

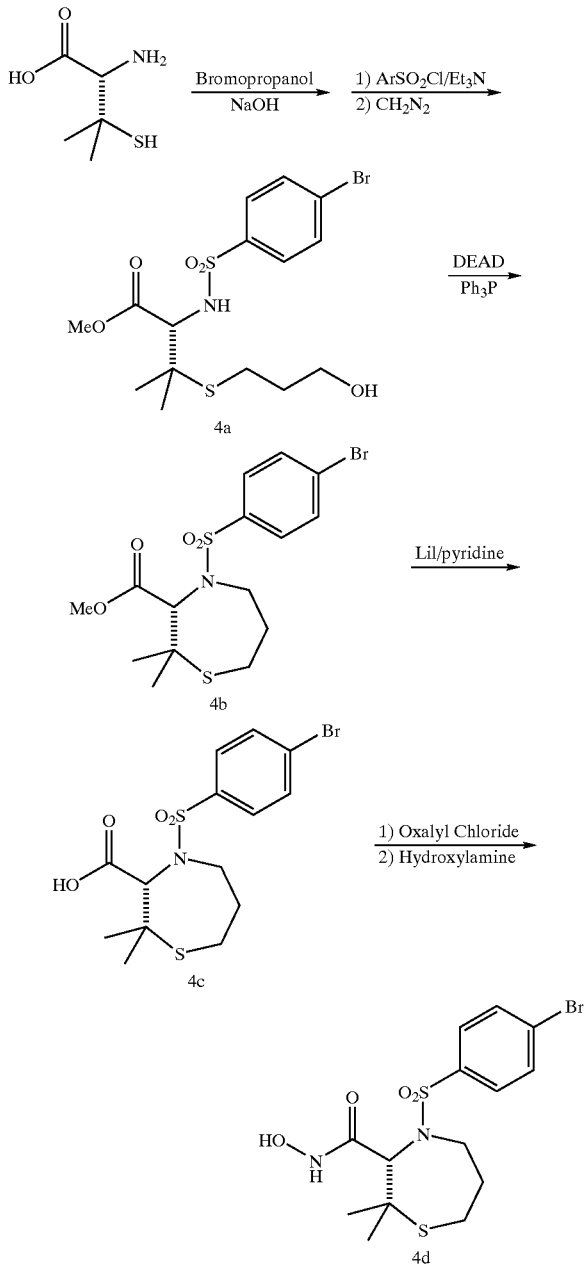

4a. Methyl N-[(4-bromophenyl)sulfonyl]-S-(2-hydroxypropyl)-D-penicillamine: D-Penicillamine (20.9 g, 134.0 mmol) in 2N NaOH (88 mL, 174.2 mmol, 1.35 equiv) is stirred at 0° C. under an Argon atmosphere. A solution of 2-bromopropanol (26.0 g, 187.7 mmol, 1.3 equiv) in ethanol (150 mL) is slowly added dropwise at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (150 mL) and water (150 mL) and stirred at room temperature. Triethylamine (40.6 g, 402 mmol, 3 equiv) is then added to the reaction mixture followed by 4-bromophenylsulfonyl chloride (41.1 g, 160.8 mmol). The resulting homogeneous solution is stirred at room temperature for 18 hours and then acidified to pH~2 with 1N HCl. The solution is poured into water and extracted with methylene chloride. The organic extracts were dried (MgSO$_4$) and concentrated to an oil under reduced pressure. The resulting oil is diluted in methanol (30 mL) and enough diazomethane in diethyl ether is added to form a yellow solution. The mixture is concentrated under reduced pressure to leave a colorless oil. Purification of the resulting methyl ester is accomplished by chromatography on silica gel using 40% ethyl acetate/60% hexane as the eluent. The desired product is obtained as a clear, colorless oil. MS (ESI): 440, 442 (M$^+$+H), 457, 459 (M$^+$+NH$_4$)

4b. Methyl 4N-[(4-bromophenyl)sulfonyl]-2,2-dimethyl-thiazepine-3-carboxylate: The methyl ester 4a (31.0 g, 70.6 mmol) in THF (400 mL) is stirred at room temperature and then triphenylphosphine (22.2 g, 84.7 mmol, 1.2 equiv) followed by diethyl azodicarboxylate (13.5 g, 77.7 mmol, 1.1 equiv) is added. The resulting solution is stirred at room temperature for 2 hours. The solvent is removed and then the thick yellow oil is diluted with methylene chloride and silica gel (60 g) is added. The solvent is removed to leave a white powder (absorb compound onto silica gel This powder is placed upon a chromatography column and eluted with 9/1 hexane/EtOAc. The desired product is obtained as a colorless oil. MS (ESI): 422, 424 (M$^+$+H), 439, 441 (M$^+$+NH$_4$)

4c. 4-[(4-bromophenyl)sulfonyl]-2,2-dimethyl-thiazepine-3-carboxylic acid: The methyl ester 4b (24.8 g, 58.9 mmol) in pyridine (350 mL) is stirred at room temperature under an argon atmosphere. Lithium iodide (107 g, 706 mmol, 12 equiv) is added and the resulting solution is heated to reflux for 3 h. The reaction Mixture is cooled to room temperature and then the solution is acidified with 1N HCl. The mixture is extracted with methylene chloride and then the organic extracts were dried (Na$_2$SO$_4$) and concentrated to an oil under reduced pressure. The oil is purified by column chromatography using 1/1 hexane/EtOAc as the eluent to provide the desired product as a light yellow oil. MS (ESI): 408, 410 (M$^+$+H), 425, 427 (M$^+$+NH$_4$).

4d. N-Hydroxy-4-[(4-bromophenyl)sulfonyl]-2,2-dimethyl-thiazepine3-carboxamide: The carboxylic acid 4c (14.65 g, 36.0 mmol) in dichloromethane (200 mL) is stirred at room temperature and then oxalyl chloride (9.4 g, 73.8 mmol, 2.05 equiv) and DMF (2.63 g, 36.0 mmol) were added. The resulting solution is stirred at room temperature for 30 minutes. In a separate flask, hydroxylamine hydrochloride (10.0 g, 144.0 mmol, 4 equiv) in THF (50 mL) and water (10 mL) is stirred at 0° C. Triethylamine (21.8 g, 216 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts were dried (Na₂SO₄) and concentrated to a solid under reduced pressure. The solid is recrystallized from acetonitrile to provide a white powder. MS (ESI): 423, 425 (M$^+$+H).

Example 5

Preparation of N-Hydroxy-S,S-dioxo-4-[(4-bromophenyl)sulfonyl]-2,2-dimethyl-thiazepine-3-carboxamide

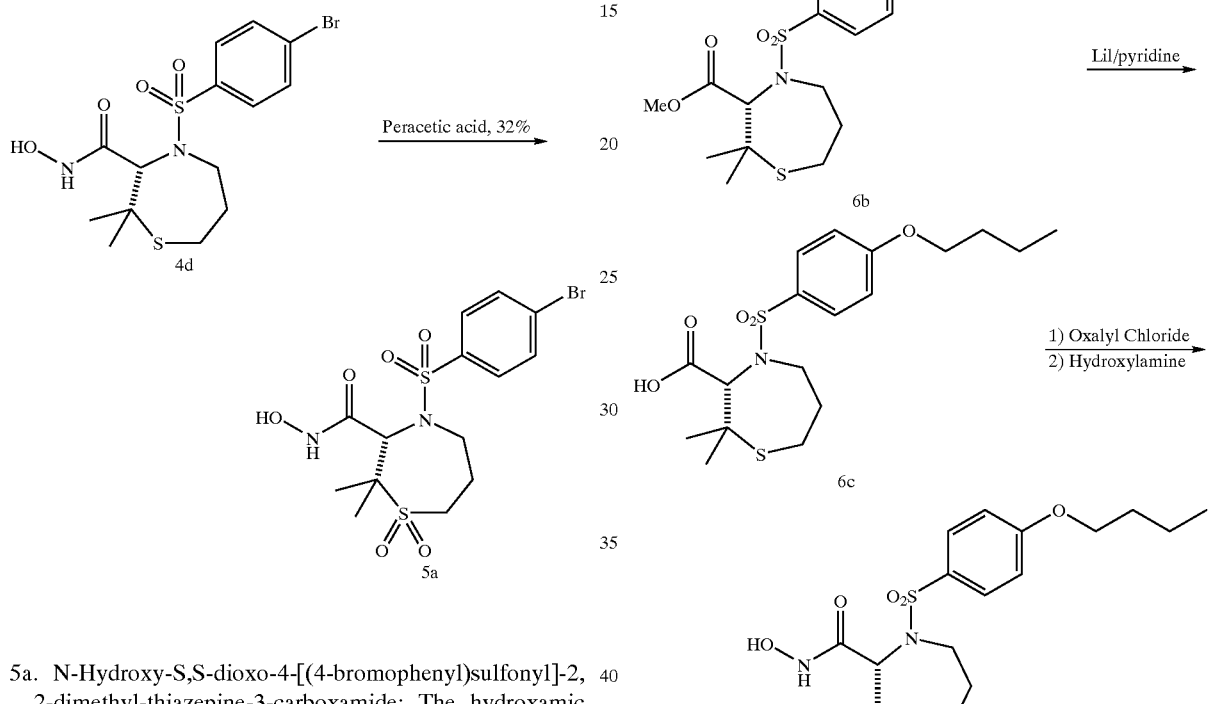

5a. N-Hydroxy-S,S-dioxo-4-[(4-bromophenyl)sulfonyl]-2,2-dimethyl-thiazepine-3-carboxamide: The hydroxamic acid (4.2 g, 9.9 mmol) is added to chloroform (50 mL). The suspension was cooled to 0° C. followed by the addition of peracetic acid (32% Aldrich solution) (6.4 mL, 29.7 mmol, 3.0 equiv). The solution becomes clear upon the addition of peracetic acid. The resulting solution is then warmed: to room temperature. After stirring overnight, the peracetic acid is removed under reduced pressure and the remaining solid is recrystalized from acetonitrile. MS (ESI): 455, 457 (M$^+$+H).

Example 6

Preparation of N-Hydroxy-4-[(4-butoxyphenyl)sulfonyl]-2,2-dimethyl-thiazepine-3-carboxamide

6a. Methyl N-[(4-butoxyphenyl)sulfonyl]-S(2-hydroxypropyl)-D-penicillamine: D-Penicillamine (2.5 g, 16.7 mmol) in 2N NaOH (18 mL, 1.35 equiv) is stirred at 0° C. under an Argon atmosphere. A solution of 2-bromopropanol (3.24 g, 23.4 mmol, 1.4 equiv) in ethanol (20 mL) is slowly added dropwise at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (30 mL) and water (30 mL) and stirred at room temperature. Triethylamine (7.0 mL, 50.1 mmol, 3 equiv) is then added to the reaction mixture followed by 4-n-butoxyphenylsulfonyl chloride (5.0 g, 20.1 mmol). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure. The resulting oil is diluted in methanol (30 mL) and enough diazomethane in diethyl ether is added to form a yellow solution. The mixture is concentrated under reduced pressure to leave a colorless oil. Purification of the resulting methyl ester is accomplished by chromatography on silica gel using 3/2 hexane/EtOAc as the eluent. The desired product is obtained as a clear, colorless oil. MS (ESI): 434 (M$^+$+H), 451 (M$^+$+NH$_4$)

6b. Methyl 4N-[(4-butoxyphenyl)sulfonyl]-2,2-dimethyl-thiazepine-3-carboxylate: The methyl ester 6a (3.3 g, 7.6 mmol) in THF (30 mL) is stirred at room temperature and then triphenylphosphine (2.39 g, 9.12 mmol, 1.2 equiv) followed by diethyl azodicarboxylate (1.45 mL, 8.36 mmol, 1.1 equiv) is added. The resulting solution is stirred at room temperature for 2 hours. The solvent is removed and then the thick yellow oil is diluted with methylene chloride and silica gel (10 g) is added. The solvent is removed to leave a white powder. This powder is placed upon a chromatography column and eluted with 9/1 hexane/EtOAc. The desired product is obtained as a colorless oil. MS (ESI): 416 (M$^+$+H), 433 (M$^+$+NH$_4$).

6c. 4-[(4-Butoxyphenyl)sulfonyl]-2,2-dimethyl-thiazepine-3-carboxylic acid: The methyl ester 6b (2.1 g, 5.06 mmol) in pyridine (50 mL) is stirred at room temperature under an argon atmosphere. Lithium iodide (8.13 g, 60.7 mmol, 12 equiv) is added and the resulting solution is heated to reflux for 3 h. The reaction mixture is cooled to room temperature and then the solution is acidified with 1N HCl. The mixture is extracted with methylene chloride and then the organic extracts are dried (Na$_2$SO$_4$) and concentrated to an oil under reduced pressure. The oil showed 95.5% purity on HPLC analysis using a solvent system of 40% A (95% water, 5% acetonotrile. 0.1% formic acid) and 60% B (20% water, 80% acetonitrile). The product is a colorless oil, which required no further purification. MS (ESI): 4402 (M$^+$+H), 419 (M$^+$+NH$_4$)

6d. N-Hydroxy-4-[(4-butoxyphenyl)sulfonyl]-2,2-dimethyl-thiazepine-3-carboxamide: The carboxylic acid 6c (1.65 g, 4.15 mmol) in dichloromethane (20 mL) is stirred at room temperature and then oxalyl chloride (1.08 g, 8.5 mmol, 2.05 equiv) and DMF (0.3 g, 4.15 mmol) are added. The resulting solution is stirred at room temperature for 30 minutes. In a separate flask, hydroxylamine hydrochloride (1.25 g, 18.0 mmol, 4 equiv) in THF (20 mL) and water (5 mL) is stirred at 0° C. Triethylamine (2.5 g, 24.9 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts are dried (Na$_2$SO$_4$) and concentrated to a solid under reduced pressure. The solid is recrystallized from CH$_3$CN/H$_2$O to provide a white powder. MS (ESI): 417 (M$^+$+H), 434 (M$^+$+NH$_4$).

Example 7

Preparation of N-hydroxy-S,S-dioxo-2,2-dimethyl-[4-(4-butoxyphenyl)sulfonyl]-thiazepine-3-carboxamide

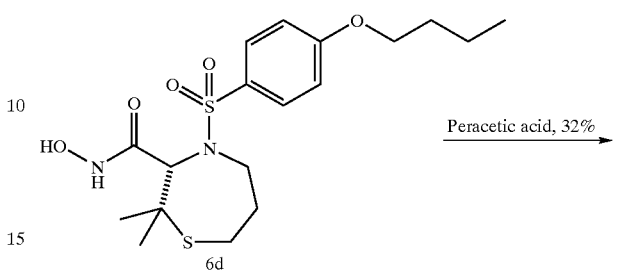

7a. N-hydroxy-S,S-dioxo-2,2-dimethyl-[4-(4-butoxyphenyl)sulfonyl]-thiazepine-3-carboxamide: The hydroxamic acid (0.50 g, 1.2 mmol) is dissolved in chloroform (10 mL) to form a suspension. The peracetic acid (0.855 g, 3.6 mmol, 3.0 equiv) is next added, and the resulting clear solution is stirred overnight. The solvents are removed under reduced pressure to leave a white solid. Purification is achieved through recrystallization with acetonitrile to form a white powder. MS (ESI): 449 (M$^+$+H), 466 (M$^+$+NH$_4$).

Example 8

Preparation of N-Hydroxy-4-[(2-methyl-4-bromophenyl)sulfonyl]-2,2-dimethyl-thiazepine-3-carboxamide 8a. Methyl N-[(2-methyl-4-bromophenyl)sulfonyl]-S(2-hydroxypropyl)-D-penicillamine: D-Penicillamine (3.0 g, 20.1 mmol) in 2N NaOH (18 mL, 1.35 equiv) is stirred at 0° C. under an Argon atmosphere. A solution of 2-bromopropanol (3.91 g, 28.1 mmol, 1.4 equiv) in ethanol (20 mL) is slowly added dropwise at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (30 mL) and water (30 mL) and stirred at room temperature. Triethylamine (8.3 mL, 60.0 mmol, 3 equiv) is then added to the reaction mixture followed by 2-methyl-4-bromophenylsulfonyl chloride (6.5 g, 24.1 mmol). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure. The resulting oil is diluted in methanol (30 mL) and enough diazomethane in diethyl ether is added to form a yellow solution. The mixture is concentrated under reduced pressure to leave a colorless oil. Purification of the resulting methyl ester is accomplished by chromatography on silica gel using 1/1 hexane/EtOAc as the eluent. The desired product is obtained as a clear, colorless oil. MS (ESI): 456, 458 (M$^+$+H), 473, 475 (M$^+$+NH$_4$)

8b. Methyl 4N-[(2-methyl-4-bromophenyl)sulfonyl]-2,2-dimethyl-thiazepine-3-carboxylate: The methyl ester 8a (4.2 g, 9.4 mmol) in THF (30 mL) is stirred at room temperature and then triphenylphosphine (2.95 g, 10.3 mmol, 1.2 equiv) followed by diethyl azodicarboxylate (1.63 mL, 11.3 mmol, 1.1 equiv) is added. The resulting solution is stirred at room temperature for 2 hours. The solvent is removed and then the thick yellow oil is diluted with methylene chloride and silica gel (10 g) is added. The solvent is removed to leave a white powder. This powder is placed upon a chromatography column and eluted with 9/1 hexane/EtOAc. The desired product is obtained as a colorless oil. MS (ESI): 436, 438 (M$^+$+H), 453, 455 (M$^+$+NH$_4$)

8c. 4-[(2-Methyl-4-bromophenyl)sulfonyl]-2,2-dimethyl-thiazepine-3-carboxylic acid: The methyl ester 8b (2.4 g. 5.45 mmol) in pyridine (75 mL) is stirred at room temperature under an argon atmosphere. Lithium iodide (8.69 g, 65.4 mmol, 12 equiv) is added and the resulting solution is heated to reflux for 3 h. The reaction mixture is cooled to room temperature and then the solution is acidified with 1N HCl. The mixture is extracted with methylene chloride and then the organic extracts are dried (Na$_2$SO$_4$) and concentrated to an oil under reduced pressure. The oil showed 97% purity on HPLC analysis using a solvent system of 40% A (95% water, 5% acetonotrile. 0.1% formic acid) and 60% B (20% water. 80% acetonitrile), the product had a retention time of 9.58. The product is a colorless oil which required no further purification. MS (ESI): 422, 424 (M$^+$+H), 439, 441 (M$^+$+NH$_4$).

8d. N-Hydroxy-4-[(2-methyl-4-bromophenyl)sulfonyl]-2,2-dimethyl-thiazepine-3-carboxamide: The carboxylic acid 8c (1.65 g, 3.9 mmol) in dichloromethane (20 mL) is stirred at room temperature and then oxalyl chloride (1.01 g, 7.9 mmol, 2.05 equiv) and DMF (0.28 g, 3.9 mmol) are added. The resulting solution is stirred at room temperature for 30 minutes. In a separate flask, hydroxylamine hydrochloride (1,1 g, 15.6 mmol, 4 equiv) in THF (20 mL) and water (5 mL) is stirred at 0° C. Triethylamine (2.4 g, 23.4 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts are dried (Na$_2$SO$_4$) and concentrated to a solid under reduced pressure. The solid is recrystallized from CH$_3$CN/H$_2$O to provide a white powder. MS (ESI): 437, 439 (M$^+$+H), 454, 456 (M$^+$+NH$_4$).

Example 9

Preparation of N-Hydroxy-6-hydroxy-2,2-dimethyl-S,S-dioxo-4[(4-methoxyphenyl)sulfonyl]-thiazepine-3(S)carboxamide

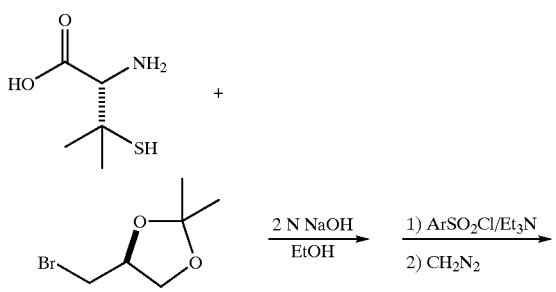

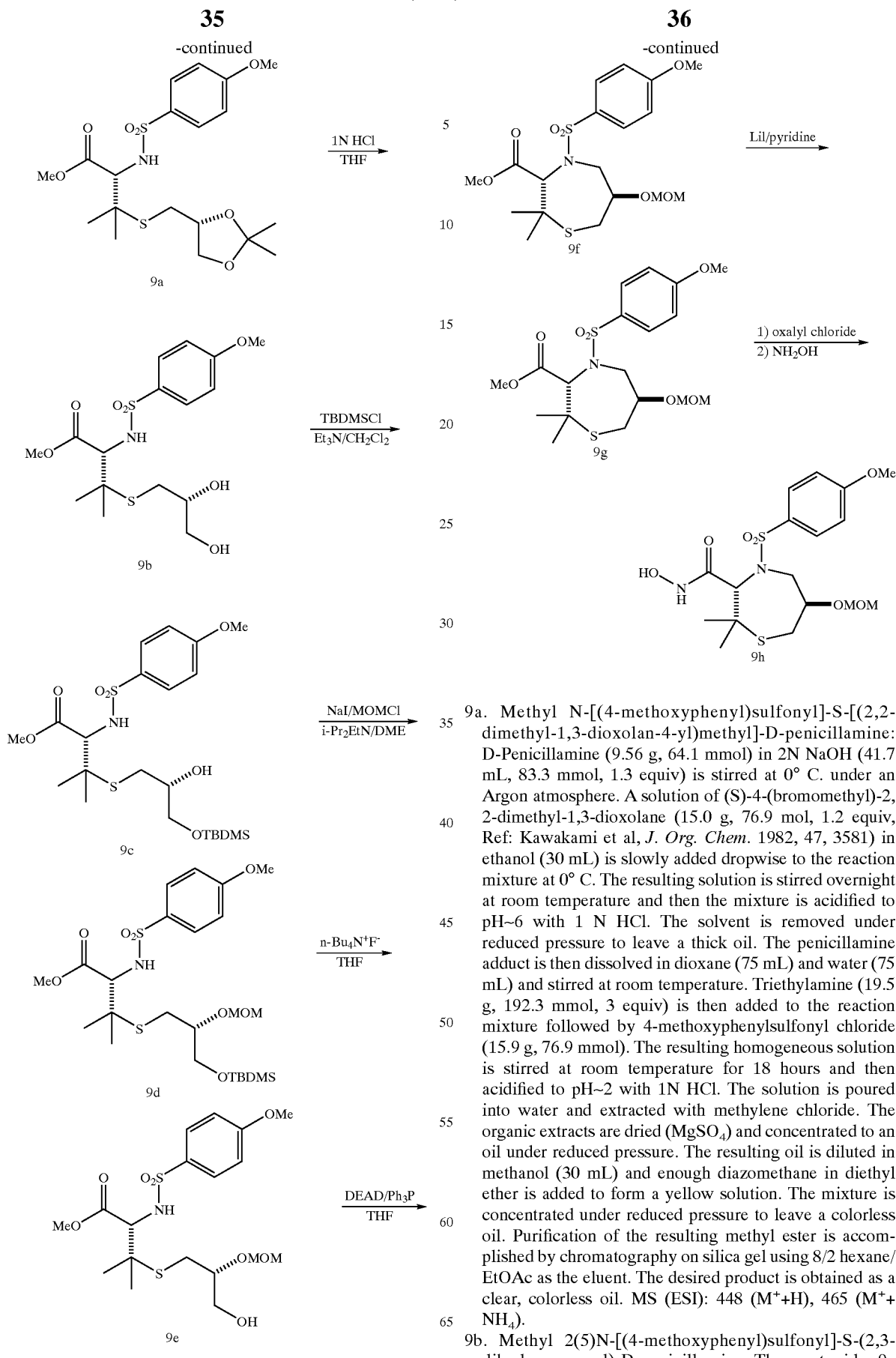

9a. Methyl N-[(4-methoxyphenyl)sulfonyl]-S-[(2,2-dimethyl-1,3-dioxolan-4-yl)methyl]-D-penicillamine: D-Penicillamine (9.56 g, 64.1 mmol) in 2N NaOH (41.7 mL, 83.3 mmol, 1.3 equiv) is stirred at 0° C. under an Argon atmosphere. A solution of (S)-4-(bromomethyl)-2,2-dimethyl-1,3-dioxolane (15.0 g, 76.9 mol, 1.2 equiv, Ref: Kawakami et al, *J. Org. Chem.* 1982, 47, 3581) in ethanol (30 mL) is slowly added dropwise to the reaction mixture at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (75 mL) and water (75 mL) and stirred at room temperature. Triethylamine (19.5 g, 192.3 mmol, 3 equiv) is then added to the reaction mixture followed by 4-methoxyphenylsulfonyl chloride (15.9 g, 76.9 mmol). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure. The resulting oil is diluted in methanol (30 mL) and enough diazomethane in diethyl ether is added to form a yellow solution. The mixture is concentrated under reduced pressure to leave a colorless oil. Purification of the resulting methyl ester is accomplished by chromatography on silica gel using 8/2 hexane/EtOAc as the eluent. The desired product is obtained as a clear, colorless oil. MS (ESI): 448 (M$^+$+H), 465 (M$^+$+NH$_4$).

9b. Methyl 2(S)N-[(4-methoxyphenyl)sulfonyl]-S-(2,3-dihydroxypropyl)-D-penicillamine The acetonide 9a (11.1 g, 24.8 mmol) in THF (50 mL) is stirred at room temperature and the 1N HCl is added. The resulting mixture is stirred overnight at room temperature until all of the starting material is consumed. The reaction mixture is concentrated to remove the THF and then the aqueous layer is extracted with methylene chloride. The organic extracts are dried (Na$_2$SO$_4$) and concentrated to an oil under reduced pressure. No further purification is performed. The product (10.0 g, 99%) is obtained as a colorless oil.

9c. Methyl N-[(4-methoxyphenyl)sulfonyl]-S-(2(S) hydroxy-3-t-butyldimethylsiloxypropyl)-D-penicillamine: The diol 9b (10.0 g, 24.5 mmol) in methylene chloride (150 mL) is stirred at room temperature and then triethylamine (2.73 g, 27 mmol, 1.1 equiv) and dimethylaminopyridine (100 mg, 0.04 equiv) is added. The t-butyldimethylsilyl chloride (3.7 g, 24.5 mmol) is added and the resulting mixture is stirred at room temperature overnight. The reaction mixture is poured into dilute sodium bicarbonate solution and extracted with methylene chloride. The organic extracts are dried (Na$_2$SO$_4$) and then concentrated to an oil under reduced pressure. Purification of the oil is accomplished by chroatography on silica gel using 7/3 hexan/EtOAc as the eluent. The product is obtained as a clear, colorless oil.

9d. Methyl N-[(4-methoxyphenyl)sulfonyl]-S-(2(S)-methoxymethoxy-3-t-butyldimethylsilyl-propyl)-D-penicillamine: Sodium iodide (12.0 g, 80 mmol, 4 equiv) is stirred in dimethoxyethane (120 mL) at room temperature and then chloromethyl methyl ether (8.2 g, 102 mmol, 5.1 equiv) is added. A brown suspension formed which became hot to touch. The resulting mixture is stirred for 10 minutes and the alcohol 9c (10.5 g, 20 mmol) and diisopropylethylamine (14.3 g, 110 mmol, 5.5 equiv) in dimethoxyethane (30 mL) is added. The mixture is stirred at room temperature for 1 h. and then heated to reflux for 4 h. The reaction mixture is poured into saturated sodium bicarbonate solution and then extracted with methylene chloride. The organic extracts re dried (Na$_2$SO$_4$) and then concentrated to an oil under reduced pressure. The oil is purified by chromatography on silica gel using 8/2 hexane/EtOAc as the eluent. The product is obtained as a yellow oil.

9e. Methyl N-[(4-methoxyphenyl)sulfonyl]-S-(2(S)-methoxymethoxy-3-hydroxypropyl)-D-penicillamine: The silyl ether 9d (3.16 g, 5.58 mmol) in THF (25 mL) is cooled to 0° C. and then tetrabutylammonium fluoride (1.0 M in THF, 14 mL, 2.5 equiv) is added. The resulting mixture is stirred at 0° C. for 30 minutes and the warmed to room temperature. The reaction mixture is stirred for an additional 3 h. The reaction mixture is poured into saturated sodium bicarbonate solution and then extracted with methylene chloride. The organic extracts are dried (Na$_2$SO$_4$) and then concentrated to an oil under reduced pressure. The oil is purified by chromatography on silica gel using 1/1 hexane/EtOAc as the eluent. The product is obtained as a clear, colorless oil.

9f. Methyl 6(S)-methozymethyl-4N-[(4-methoxyphenyl) sulfonyl]-2,2-dimethyl-thiazepine-3(S)-carboxylate: The methyl ester 9e (1.9 g, 4.3 mmol) in THF (15 mL) is stirred at room temperature and then triphenylphosphine (1.35 g, 5.16 mmol, 1.2 equiv) followed by diethyl azodicarboxylate (0.82 g 4.73 mmol. 1.1 equiv) is added. The resulting solution is stirred at room temperature for 2 hours. The solvent is removed and then the thick yellow oil is diluted with methylene chloride and silica gel (20 g) is added. The solvent is removed to leave a white powder. This powder is placed upon a chromatography column and eluted with 8/2 hexane/EtOAc. The desired product is obtained as a colorless oil. MS (ESI): 434 (M$^+$+H), 451 (M$^+$+NH$_4$).

9g. 6-Methoxymethyl-4-[(4-methoxyphenyl)sulfonyl]-2,2-dimethyl-thiazepine-3(S)-carboxylic acid: The methyl ester 9f (2.2 g, 5.07 mmol) in pyridine (40 mL) is stirred at room temperature under an argon atmosphere. Lithium iodide (8.15 g, 61.9 mmol, 12 equiv) is added and the resulting solution wa heated to reflux for 3 h. The reaction mixture wa cooled to room temperature and then the solution wa acidified with 1N HCl. The mixture wa extracted with methylene chloride and then the organic extracts are dried (Na$_2$SO$_4$) and concentrated to an oil under reduced pressure. The oil wa purified by column chromatography using 1/1 hexane/EtOAc as the eluent to provide the desired product as a light yellow oil. MS (ESI): 420 (M$^+$+H), 437 (M$^+$+NH$_4$), 442 (M++Na).

9h. N-Hydroxy-6-methozymethyl-4-[(4-methoxyphenyl) sulfonyl]-2,2-dimethyl-thiazepine-3-carboxamide: The carboxylic acid 9g (2.35 g, 5.6 mmol) in acetonitrile (15 mL) is stirred at room temperature and then oxalyl chloride (1.46 g, 11.5 mmol, 2.05 equiv) and DMF (0.41 g, 5.6 mmol) are added. The resulting solution is stirred at room temperature for 30 minutes. In a separate flask, hydroxylamine hydrochloride (1.56 g, 22.4 mmol, 4 equiv) in THF (10 mL) and water (2 mL) is stirred at 0° C. Triethylamine (3.40 g, 33.6 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is acidified with 1 N HCl and then extracted with dichloromethane. The organic extracts are dried (Na$_2$SO$_4$) and concentrated to a solid under reduced pressure. The solid is purified by reverse phase HPLC using 60/40 water/acetonitrile as the eluent to provide a white powder. MS (ESI): 373 (M$^+$+H).

Example 10

Preparation of N-Hydroxy-S,S-oxo-6-hydroxy-4-[(4-methoxyphenyl)sulfonyl]-2,2-dimethyl-thiazepine-3-carboxamide

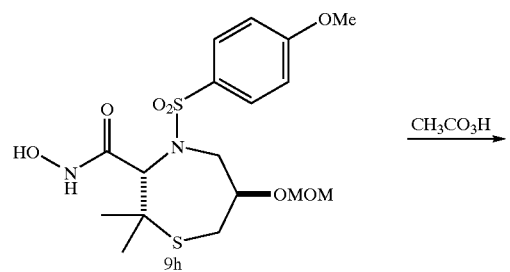

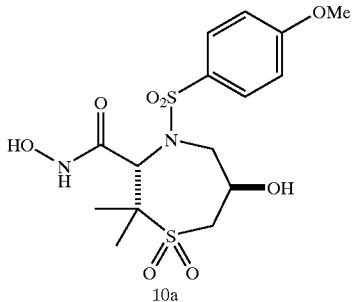

10a

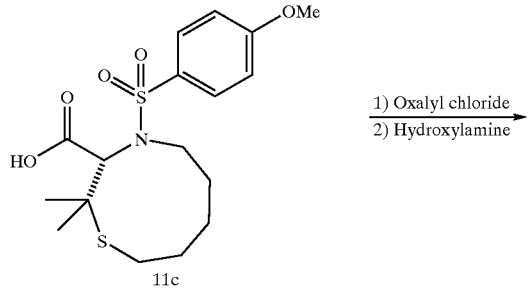

10a. N-Hydroxy-S,S-dioxo-6-hydroxy-4-[(4-methoxyphenyl)sulfonyl]-2,2-dimethyl-thiazepine-3-carboxamide: The hydroxamic acid 9h (1.30 g, 2.99 mmol) is dissolved in chloroform (50 mL) and the mixture is stirred at room temperature. A 32% solution of peracetic acid (3.03 mL. 11.97 mmloes, 4.0 equiv) is added and the resulting mixture is stirred at room temperature. The solvent and remaining peracetic acid is removed under reduced pressure to leave the desired product as a white solid. The solid is recrystallized from acetonitrile to provide the product as a white crystalline solid. MS (ESI): 423 (M+H$^-$).

Example 11

Preparation of 3(S)N-Hydroxy-2,2-dimethyl-4-[(4-methoxyphenyl)sulfonyl]octahydro-1,4-thiazonine-3-carboxamide

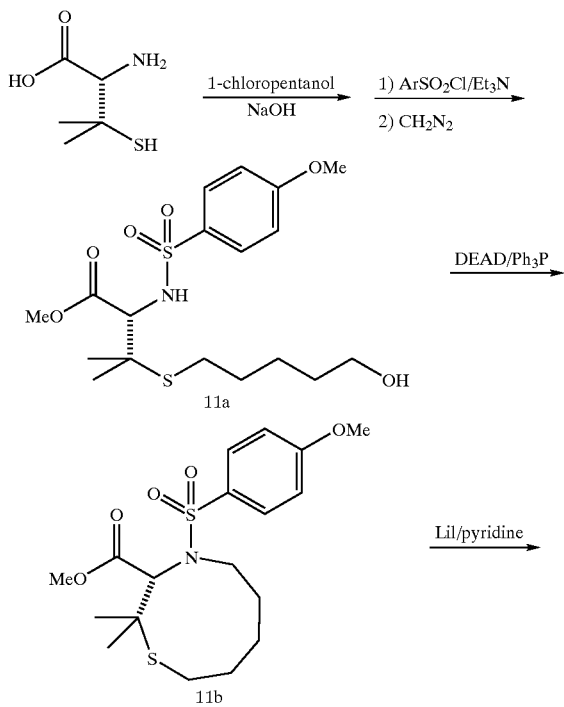

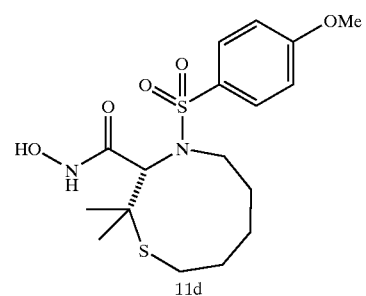

11d

11a. Methyl N-[(4-methoxyphenyl)sulfonyl]-S(2-hydroxypentyl)-D-penicillamine: D-Penicillamine (5.0 g, 33.5 mmol) in 2N NaOH (21.8 mL, 43.6 mmol, 1.3 equiv) is stirred at 0° C. under an Argon atmosphere. A solution of 1-chloropentanol (4.92 g, 40.2 mmol, 1.2 equiv) in ethanol (30 mL) is slowly added dropwise at 0° C. The resulting solution is stirred overnight at room temperature and then the mixture is acidified to pH~6 with 1 N HCl. The solvent is removed under reduced pressure to leave a thick oil. The penicillamine adduct is then dissolved in dioxane (100 mL) and water (100 mL) and stirred at room temperature. Triethylamine (10.2 g, 100 mmol, 3 equiv) is then added to the reaction mixture followed by 4-methoxyphenylsulfonyl chloride (7.62 g, 36.9 mmol, 1.1 equiv). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure. The resulting oil is diluted in methanol (20 mL) and enough diazomethane in diethyl ether is added to form a yellow solution. The mixture is concentrated under reduced pressure to leave a colorless oil. Purification of the resulting methyl ester is accomplished by chromatography on silica gel using 6/4 hexane/EtOAc as the eluent. The desired product is obtained as a clear, colorless oil. MS (ESI): 420 (M$^+$+H), 437 (M$^+$+NH$_4$).

11b. Methyl 3(S)-N-Hydroxy-2,2-dimethyl-4-[(4-methoxyphenyl)sulfonyl]octahydro-1,4-thiazonine-3-carboxylate: The methyl ester 11a (2.1 g, 5.0 mmol) in THF (50 mL) is stirred at room temperature and then triphenylphosphine (1.58 g, 6.0 mmol, 1.2 equiv) followed by diethyl azodicarboxylate (0.96 g, 5.50 mmol, 1.1 equiv) is added. The resulting solution is stirred at room temperature for 18 hours. The solvent is removed and then the thick yellow oil is diluted with methylene chloride and silica gel (15 g) is added. The solvent is removed to leave a white powder. This powder is placed upon a chromatography column and eluted with 8/2 hexane/EtOAc. The desired product is obtained as a colorless oil. MS (ESI): 402 (M$^+$+H), 419 (M$^+$+NH$_4$).

11c. 3(S)-N-Hydroxy-2,2-dimethyl-4-[(4-methoxyphenyl)sulfonyl]octahydro-1,4-thiazonine-3-carboxylic acid: The methyl ester 11b (0.44 g, 1.10 mmol) in pyridine (10 mL) is stirred at room temperature under an argon atmosphere. Lithium iodide (1.76 g, 13.1 mmol, 12 equiv) is added and the resulting solution is heated to reflux for 5 h. The reaction mixture is cooled to room temperature and then the solution is acidified with 1N HCl. The mixture is extracted with methylene chloride and then the organic extracts are dried (Na$_2$SO$_4$) and concentrated to an oil under reduced pressure. The oil is purified by column chromatography using 1/1 hexane/EtOAc as the eluent to provide the desired product as a light yellow oil. MS (ESI): 388 (M$^+$+H), 405 (M$^+$+NH$_4$).

11d. 3(S)-N-Hydroxy-2,2-dimethyl-4-[(4-methoxyphenyl)sulfonyl]octahydro-1,4thiazonine-3-carboxamide: The carboxylic acid 11c (392 mg, 1.01 mmol) in dichloromethane (10 mL) is stirred at room temperature and then oxalyl chloride (0.263 g, 2.07 mmol, 2.05 equiv) and DMF (73.9 mg, 1.01 mmol) are added. The resulting solution is stirred at room temperature for 30 minutes. In a separate flask, hydroxylamine hydrochloride (3.3 g, 47.5 mmol, 4 equiv) in THF (50 mL) and water (10 mL) is stirred at 0° C. Triethylamine (615 mg, 6.06 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts are dried (Na$_2$SO$_4$) and concentrated to a solid under reduced pressure. The solid is recrystallized from CH$_3$CN to provide a white powder. MS (ESI): 378 (M$^+$+NH$_4$), 361 (M$^+$+H).

Example 12

Preparation of N-Hydroxy-2-methyl-4N-[(4-methoxyphenyl)sulfonyl]-thiazepine-3-carboxamide

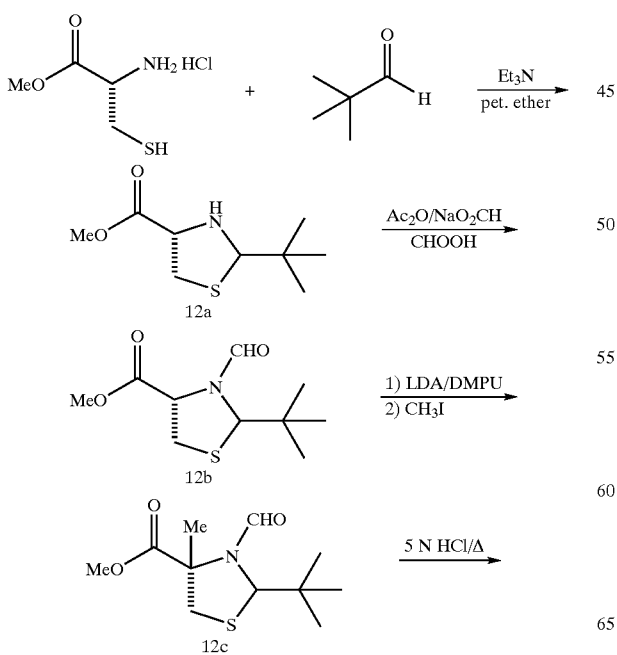

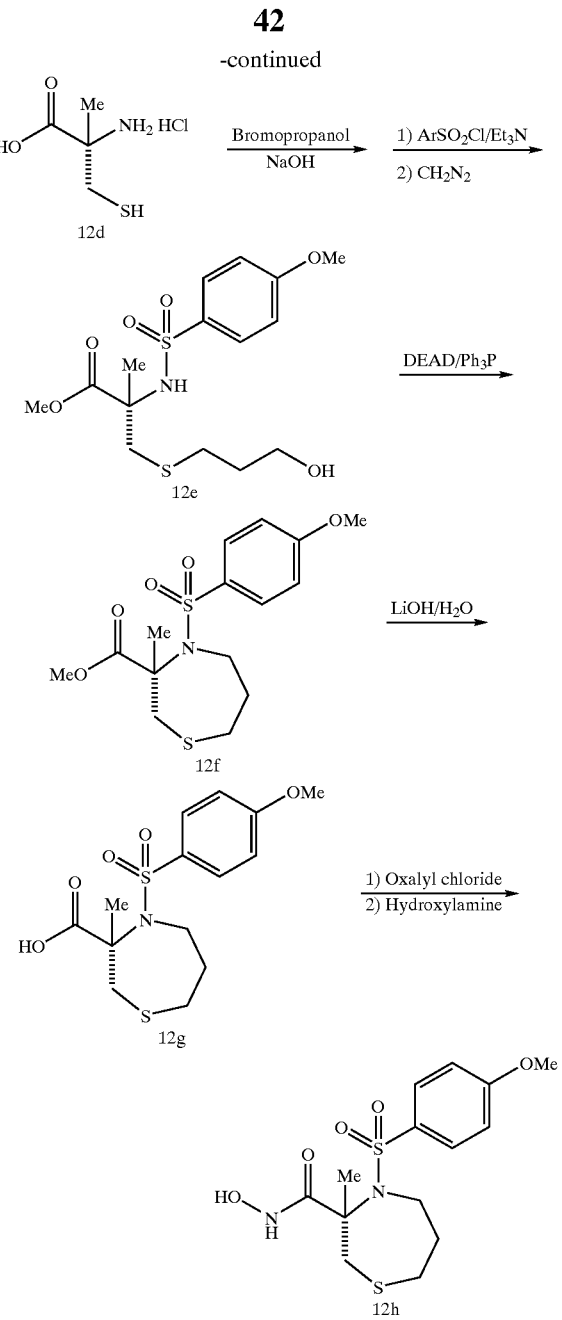

12a. 4(S)-Methyl 2-tert-butyl-1,3-thiazolidine-4-carboxylate (1): D-Cysteine methyl ester hydrochloride (12.9 g, 75.2 mmol) and trimethylacetaldehyde (7.12 g, 82.7 mmol) in petroleum ether (150 mL) was stirred at room temperature and then triethylamine (8.37 g, 82.7 mmol) was added dropwise over a five minute period. The resulting heterogeneous mixture was stirred for 16 h. at reflux and water was removed with the aid of a Dean-Stark trap. The reaction mixture was cooled to room temperature and then filtered. The residue was washed with diethyl ether. The resulting filtrate was concentrated to leave 14.87 g (97%) of the desired product as a light yellow oil.

12b. 2s,4S-Methyl 2-tert-butyl-1,3-thiazolidine-3-formyl-4-carboxylate (2): The thiazolidine (14.8 g, 72.8 mmol) in formic acid (110 mL) and saodium formate (5.45 g, 80 mmol, 1.1 equiv) was stirred at 0° C. and then acetic anhydide (22.3 g, 218 mmol, 3 equiv) was added dropwise over a 45 minute period. The resulting solution was then warmed to room temperature and stirred overnight. The mixture was concentrated under reduced pressure to leave a yellow oil. The oil was carefully neutralized with saturated sodium bicarbonate solution and then extracted with diethyl ether (3×200 mL). The combined ether extracts were dried ($Na_2SO_4$) and then concentrated to an oil under reduced pressure. The oil (13.2 g, 79%) crystallized upon standing.

12c. 2S,4S-Methyl 2-tert-butyl-1,3-thiolidine-3-formyl-4-methyl-4-carboxylate (3): A solution of n-butyllithium (1.6 M, 25.8 mL, 41.2 mmol, 1.06 equiv) was added dropwise to a cold (−78° C.) solution of diisopropylamine (5.9 g, 58.4 mmol, 1.5 equiv) in THF (180 mL). The resulting solution was stirred at −78° C. for 10 minutes. The DMPU (1,3-dimethyl-3,4,5,6-tetrahydro-2(1H)-pyrimidone, 27 mL) was next added and the now blue solution was stirred at −78° C. for 1 h. The reaction mixture was cooled to −90° C. and then the thiazolidine (9.0 g 38.9 mmol) in THF (10 mL) was slowly added. The mixture was stirred for an additional 0.75 h at −90° C. and then methyl iodide (6.63 g, 46.7 mmol, 1.2 equiv) was added over 5 minutes. The reaction mixture was stirred at −90° C. for 2 h. and then warmed to room temperature. The solvent was removed to leave an oil which was poured into brine (200 mL) and extracted with diethyl ether (3×200 mL). The combined organic extracts were dried ($Na_2SO_4$) and then concentrated to an oil under reduced pressure. Purification of the oil was accomplished by chromatography on silica gel using 9/1 hexane/EtOAc as the eluent. The product (5.90 g, 62%) was obtained as a clear, colorless oil.

12d. (S)-2-Methylcysteine hydrochloride (4): The methyl ester (6.0 g, 24.6 mmol) was added to 5N HCl (110 mL) and the resulting mixture was heated to reflux for 3 days. The mixture was then cooled to room temperature and the solvent was removed under reduced pressure to leave 3.62 g (87%) of a yellow solid.

12e. Methyl N-[(4-methoxyphenyl)sulfonyl]-S(2-hydroxyethyl)-2-methyl-D-cysteine (5) D-Penicillamine (14.9 g, 0.1 mol) in 2N NaOH (65 mL, 0.13 mol, 1.3 equiv) was stirred at 0° C. under an Argon atmosphere. A solution of 2-bromopropanol (15 g, 0.12 mol, 1.2 equiv) in ethanol (100 mL) was slowly added dropwise at 0° C. The resulting solution was stirred overnight at room temperature and then the mixture was acidified to pH~6 with 1 N HCl. The solvent was removed under reduced pressure to leave a thick oil. The penicillamine adduct was then dissolved in dioxane (200 mL) and water (200 mL) and stirred at room temperature. Triethylamine (29.8 g, 0.295 mol, 3 equiv) was then added to the reaction mixture followed by 4-methoxyphenylsulfonyl chloride (22.3 g, 0.108 mol, 1.1 equiv). The resulting homogeneous solution was stirred at room temperature for 18 hours and then acidified to pH~2 with 1N HCl. The solution was poured into water and extracted with methylene chloride. The organic extracts were dried ($MgSO_4$) and concentrated to an oil under reduced pressure. The resulting oil was diluted in methanol (30 mL) and enough diazomethane in diethyl ether was added to form a yellow solution. The mixture was concentrated under reduced pressure to leave a colorless oil. Purification of the resulting methyl ester was accomplished by chromatography on silica gel using 1/1 hexane/EtOAc as the eluent. The desired product was obtained as a clear, colorless oil.

12f. Methyl 2-methyl-4N-[(4-methoxyphenyl)sulfonyl]-thiazepine-3-carboxylate (6) The methyl ester (10.8 g, 28.6 mmol) in THF (200 mL) was stirred at room temperature and then triphenylphosphine (9.0 g, 34.3 mmol, 1.2 equiv) followed by diethyl azodicarboxylate (5.48 g, 31.5 mmol, 1.1 equiv) was added. The resulting solution was stirred at room temperature for 2 hours. The solvent was removed and then the thick yellow oil was diluted with methylene chloride and silica gel (30 g) was added. The solvent was removed to leave a white powder. This powder was placed upon a chromatography column and eluted with 8/2 hexane/EtOAc. The desired product was obtained as a colorless oil. MS (ESI): 360 ($M^+$+H), 377 ($M^+$+$NH_4$).

12g. 2-Methyl-4N-[(4-methoxyphenyl)sulfonyl]-thiazepine-3-carboxylic acid The methyl ester (9.5 g. 26.4 mmol) in pyridine 150 mL) was stirred at room temperature under an argon atmosphere. Lithium iodide (42.4 g, 317 mmol, 12 equiv) was added and the resulting solution was heated to reflux for 3 h. The reaction mixture was cooled to room temperature and then the solution was acidified with 1N HCl. The mixture was extracted with methylene chloride and then the organic extracts were dried ($Na_2SO_4$) and concentrated to an oil under reduced pressure. The oil was purified by column chromatography using 1/1 hexane/EtOAc as the eluent to provide the desired product as a light yellow oil.

12h. N-Hydroxy-2-methyl-4N-[(4-methoxyphenyl)sulfonyl]-thiazepine-3-carboxamide The carboxylic acid (4.1 g, 11.8 mmol) in dichloromethane (50 mL) was stirred at room temperature and then oxalyl chloride (3.09 g, 24.3 mmol, 2.05 equiv) and DMF (0.87 g, 11.8 mmol) were added. The resulting solution was stirred at room temperature for 30 minutes. In a separate flask, hydroxylamine hydrochloride (3.3 g, 47.5 mmol, 4 equiv) in THF (50 mL) and water (10 mL) was stirred at 0° C. Triethylamine (7.16 g, 70.8 mmol, 6 equiv) was added and the resulting solution was stirred at 0° C. for 15 minutes. The acid chloride solution was next added to the hydroxylamine solution at 0° C. and the resulting mixture was allowed to stir overnight at room temperature. The reaction mixture was next acidified with 1 N HCl and then extracted with dichloromethane. The organic extracts were dried ($Na_2SO_4$) and concentrated to a solid under reduced pressure. The solid was recrystallized from $CH_3CN/H_2O$ to provide a white powder. MS (ESI): 378 ($M^+$+$NH_4$), 361 ($M^+$+H).

Example 13

Preparation of N-Hydroxy-1-(4-methoxyphenylsulfonyl)-3,3-dimethyl-hexahydro-1H-azepine-2-carboxamide

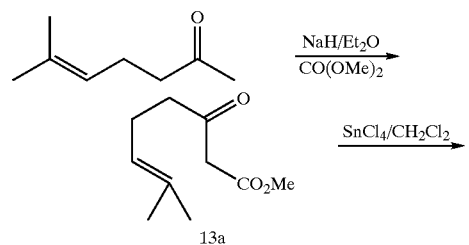

13a

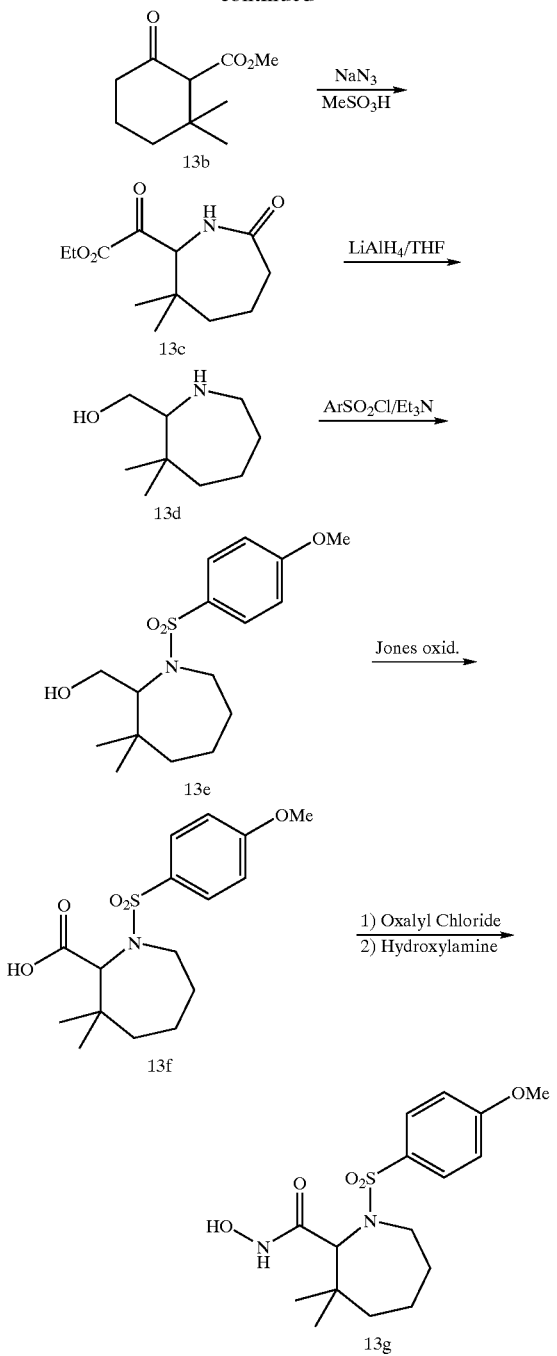

13a. Methyl 7-methyl-3-oxo-6-octenoate: In a dry flask, sodium hydride (17.44 g, 436 mmol) was added under argon and rinsed several times with hexane to remove the mineral oil. A solution of of dimethylcarbonate (35.66 g, 396 mmol) in ether (60 mL)was added. The suspension was stirred and heated to reflux. Next, 6-methyl-5-hepten-2-one (25.2 g, 198 mmol) was added dropwise until hydrogen began to evolve. The remaining ketone was added very slowly over a period of several hours at reflux. Once the addition was complete, the solution was stirred for an additional 2 hours, and then allowed to stand at room temperature overnight. The mixture was cooled in an ice bath and a solution of methanol (40 mL) in ether (200 mL) was added cautiously. The reaction mixture remained in the ice bath for 1 hour until all bubbling ceased. The reaction mixture was then stirred at room temperature for 2 hours. The resulting suspension was poured onto ice (320 g) and concentrated HCl (80 mL). The solution was extracted several times with ether, the organic layers were washed with sodium bicarbonate and dried over magnesium sulfate and concetrated under reduced pressure to form an oil. Purification was achieved through distillation, the product distilled at 75° C. to 90° C. The product was obtained as a clear pale yellow oil. MS (ESI): 185 (M$^+$+H), 202 (M$^+$+NH$_4$).

13b. Methyl 2,2-dimethyl-6-oxo-cycloexanecarboxylate: The methyl ester 13a (16.3 g, 88.6 mmol) was dissolved in methylene chloride (600 mL) and cooled to 0° C., followed by the addition of stannic chloride (34.5 g, 132.8 mmol). The reaction mixture stirred at room temperature overnight. The reaction was diluted with ether (1000 mL) and washed with 1N HCl several times and some water, the organic layer was dried over magnesium sulfate and evaporated down under educed pressure. The residue was purified on silica gel using eluents of hexane: ethyl acetate (95:5). MS (ESI): 185 (M$^+$+H), 202 (M$^+$+NH$_4$).

13c. 6,6-Dimethyl-7-carbomethoxy-tetrahydro-2(3H)-azepinone: The keto ester 13b (7.3 g, 39.7 mmol) is dissolved in chloroform (180 mL) and cooled to 0° C. Methanesulfonic acid (38.1 g, 397 mmol) was added followed by the addition of sodium azide. The reaction mixture was stirred at room temperature for 30 minutes and then heated to reflux for 5 hours. Ice was added to the reaction mixture and stirred for several minutes, this was followed by the addition of ammonium hydroxide until the reaction became basic. The mixture is then extracted with methylene chloride, and the organic layers are dried (MgSO$_4$) and concentrated under reduced pressure to an oil. MS (ESI): 200 (M$^+$+H).

13d. 2-Hydroxymethyl-3,3-dimethyl-hexahydro-1H-azepine: The ketone 13c (3.75 g, 18.9 mmol) is dissolved in THF (100 mL) under an argon atmosphere at room temperature. Lithium aluminum hydride (1.5 g, 37.7 mmol, 2 equiv) was next added slowly to the reaction mixture. The reaction mixture was heated to reflux for 5 hours. The mixture was quenched by the slow, dropwise addition of ethyl acetate until bubbling of the reaction mixture ceased. Then, water (1.5 mL) was added to the solution. A 15% NaOH (1.5 mL) was next added followed by water (3.0 mL). The resulting heterogeneous mixture is then filtered, and the remaining organic layer is diluted with water and extracted with ether. The organic layers are dried over sodium sulfate and concentrated under reduced pressure. MS (ESI): 158 (M$^+$+H).

13e. 1-[(4-Methoxyphenyl)sulfonyl]-2-hydroxymethyl-3,3-dimethyl-hexahydro-1H-azepine: The alcohol 13d (2.9 g, 18.9 mmol) was dissolved in a 1:1 mixture of water and p-dioxane (100 mL), followed by the addition of 4-methoxyphenylsulfonyl chloride (4.7 g, 22.6 mmol) and triethylamine (7.86 mL, 56.5 mmol). The reaction mixture was stirred overnight. The reaction was quenched and acidified with 1N HCl to a pH~2. The mixture was then diluted with water and extracted with methylene chloride. The organic layers were dried over magnesium sulfate, and concentrated under reduced pressure. The compound was purified by silica gel chromatography using hexane: ethyl acetate (3:2) as the eluent. MS (ESI): 328 (M$^+$+H), 345 (M$^+$+NH$_4$).

13f. 1-[(4-Methoxyphenyl)sulfonyl]-3,3-dimethyl-hexahydro-1H-azepine-2-carboxylic acid: The alcohol 13e (0.40 g, 1.22 mmol) is dissolved in acetone (50 mL)

and freshly prepared 8N Jones reagent is added until the solution sustains an orange/brown color as opposed to a green color. The reaction mixturE is then stirred overnight. Isopropanol is added to quench the excess Jones reagent and a green solid precipitates out of solution. The solid is filtered through celite, and the liquid is concentrated under reduced pressure. The residue is then dissolved in chloroform and washed with water several times. The organic layer is dried over magnesium sulfate, and concentrated under reduced pressure. The product is carried: forward with no further purification. MS (ESI): 342 ($M^+ + H$), 359 ($M^+ + NH_4$).

13g. N-Hydroxy-1-[(4-methoxyphenyl)sulfonyl]-3,3-dimethyhexahydro-1H-azepine-2-carboxamide: The carboxylic acid 13f (0.37 g, 1.07 mmol) in dichloromethane (10 mL) was stirred at room temperature and then oxalyl chloride (0.28 g, 2.2 mmol, 2.05 equiv) and DMF (0.08 g, 4.15 mmol) were added. The resulting solution was stirred at room temperature for 30 minutes. In a separate flask, hydroxylamine hydrochloride (0.3 g, 4.28 mmol, 4 equiv) in THF (10 mL) and water (2 mL) was stirred at 0° C. Triethylamine (0.65 g, 6.42 mmol, 6 equiv) was added and the resulting solution was stirred at 0° C. for 15 minutes. The acid chloride solution was next added to the hydroxylamine solution at 0° C. and the resulting mixture was allowed to stir overnight at room temperature. The reaction mixture was next acidified with 1 N HCl and then extracted with dichloromethane. The organic extracts were dried ($Na_2SO_4$) and concentrated to a solid under reduced pressure. The solid was recrystallized from $CH_3CN/H_2O$ to provide the desired product as a white powder. MS (ESI): 357 ($M^+ + H$).

Example 14

Preparation of N-Hydroxy-1[(4-methoxyphenyl) sulfonyl]-hexahydro-1H-azepine-2-carboxamide

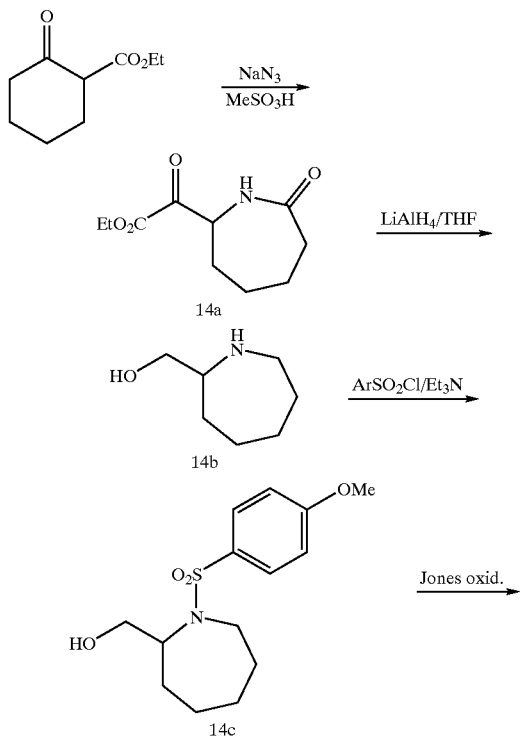

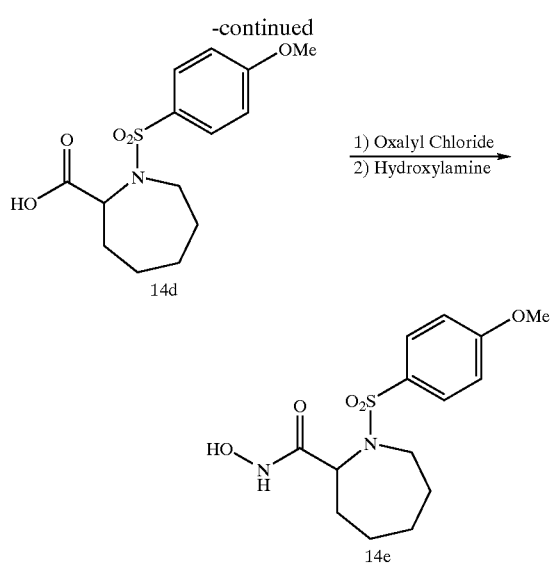

14a. 7-Carboxmethoxy-tetrahydro-2(3H)-azepinone: The ethyl 2-cyclohexanone carboxylate (15.0 g 88.12 mmol) is dissolved in chloroform (200 mL) and cooled to 0° C. Methanesulfonic acid (84.7 g, 881.2 mmol) was added followed by the addition of sodium azide. The reaction mixture was stirred at room temperature for 30 minutes and then heated to reflux for 5 hours. Ice was added to the reaction mixture and the resulting solution was stirred for several minutes. Ammonium hydroxide was added until the reaction is made basic. The mixture is extracted with methylene chloride, and the organic layers are dried ($MgSO_4$) and concentrated under reduced pressure to an oil. MS (ESI): 186 ($M^+ + H$).

14b. 2-Hydroxymethyl-hexahydro-1H-azepine: The amide 14a (5.0 g, 27.0 mmol) is dissolved in THF (100 mL) under an argon atmosphere at room temperature. Lithium aluminum hydride (2.0 g, 54.0 mmol, 2 equiv) was then cautiously added. The reaction mixture was heated to reflux for 5 hours. The mixture was quenched by the slow, dropwise addition of ethyl acetate until bubbling of the reaction mixture ceased. Then, water (2.0 mL) was added to the solution. A 15% NaOH (2.0 mL) was next added followed by water (5.0 mL). The resulting homogeneous solution is filtered, and the remaining organic layer is diluted with water and extracted with ether. The organic layers are dried over sodium sulfate and concentrated under reduced pressure.

14c. 1-[(4-Methoxyphenylsulfonyl]-2-hydroxymethyl-hexahydro-1H-azepine: The alcohol 14b (3.0 g, 23.5 mmol) was dissolved in a 1:1 mixture of water and p-dioxane (100 mL) followed by the addition of 4-methoxyphenylsulfonyl chloride (5.8 g, 28.2 mmol) and triethylamine (9.8 mL, 70.5 mmol). The reaction mixture was left to stir overnight. The reaction was quenched and acidified with 1N HCl to a pH~2. The reaction mixture was then diluted with water and extracted with methylene chloride. The organic layers were dried over magnesium sulfate, and concentrated under reduced pressure. The compound was purified by silica gel chromatography using hexane: ethyl acetate (2:1) as the eluent. MS (ESI): 300 ($M^+ + H$), 317 ($M^+ + NH_4$).

14d. 1[(4-Methoxyphenyl)sulfonyl]-hexahydro-1H-azepine-2-carboxylic acid: The alcohol 14c (1.3 g, 4.35 mmol) is dissolved in acetone (100 mL) at 0° C. and freshly prepared 8N Jones reagent is added until the solution sustains an orange/brown color as opposed to a green color. The resulting mixture is then stirred overnight. Isopropanol is added to quench the excess Jones reagent and a green solid precipitates out. The solid is filtered through celite, and the liquid is concentrated under reduced pressure. The residue is then dissolved in chloroform and washed with water several times. The organic layer is dried over magnesium sulfate, and concetrated under reduced pressure. The product is carried forward with no further purification. MS (ESI): 314 ($M^+$+H), 331 ($M^+$+$NH_4$).

14e. N-Hydroxy-1-[(4-methoxyphenyl)sulfonyl]-hexahydro-1H-azepine-2-carboxamide: The carboxylic acid 14d (1.11 g, 3.56 mmol) in dichloromethane (25 mL) was stirred at room temperature and then oxalyl chloride (0.93 g, 7.2 mmol, 2.05 equiv) and DMF (0.260 g, 3.56 mmol) were added. The resulting solution was stirred at room temperature for 30 minutes. In a separate flask, hydroxylamine hydrochloride (0.99 g, 14.24 mmol, 4 equiv) in THF (15 mL) and water (8 mL) was stirred at 0° C. Triethylamine (2.15 g, 21.4 mmol, 6 equiv) was added and the resulting solution was stirred at 0° C. for 15 minutes. The acid chloride solution was next added to the hydroxylamine solution at 0° C. and the resulting mixture was allowed to stir overnight at room temperature. The reaction mixture was next acidified with 1 N HCl and then extracted with dichloromethane. The organic extracts were dried ($Na_2SO_4$) and concentrated to a solid under reduced pressure. The solid was recrystallized from $CH_3CN/H_2O$ to provide a white powder. MS (ESI): 429 ($M^+$+H).

Examples 15–101

The following (where W is nil) compounds are made using the methods described and exemplified above.

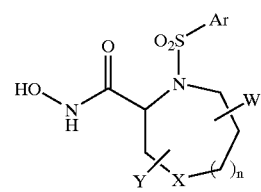

| | Y | X | W | Ar | n |
|---|---|---|---|---|---|
| Example 15 | 3,3-($CH_3$—)$_2$ | S | H | 4-$NO_2$—$C_6H_4$— | 1 |
| Example 16 | 3,3-($CH_3$—)$_2$ | S | H | 4-i-BuO—$C_6H_4$— | 1 |
| Example 17 | 3,3-($CH_3$—)$_2$ | S | H | 4-($C_6H_5$)O—$C_6H_4$— | 1 |
| Example 18 | 3,3-($CH_3$—)$_2$ | S | H | 4-(4-F—$C_6H_4$)O—$C_6H_4$— | 1 |
| Example 19 | 3,3-($CH_3$—)$_2$ | S | H | 4-(4-Cl—$C_6H_4$)O—$C_6H_4$— | 1 |
| Example 20 | 3,3-($CH_3$—)$_2$ | S | H | 4-(4-Br—$C_6H_4$)O—$C_6H_4$— | 1 |
| Example 21 | 3,3-($CH_3$—)$_2$ | S | H | 4-(4-Me—$C_6H_4$)O—$C_6H_4$— | 1 |
| Example 22 | 3,3-($CH_3$—)$_2$ | S | H | 4-(4-MeO—$C_6H_4$)O—$C_6H_4$— | 1 |
| Example 23 | 3,3-($CH_3$—)$_2$ | S | H | 4-(4-CN—$C_6H_4$)O—$C_6H_4$— | 1 |
| Example 24 | 3,3-($CH_3$—)$_2$ | S | H | 4-(4-$Me_2$N—$C_6H_4$)O—$C_6H_4$— | 1 |
| Example 25 | 3,3-($CH_3$—)$_2$ | S | H | 4-EtO—$C_6H_4$— | 1 |
| Example 26 | 3,3-($CH_3$—)$_2$ | S | H | 4-i-PrO—$C_6H_4$— | 1 |
| Example 27 | 3,3-($CH_3$—)$_2$ | S | H | 4-n-PrO—$C_6H_4$— | 1 |
| Example 28 | 3,3-($CH_3$—)$_2$ | S | H | 2-$CH_3$-4-Br—$C_6H_3$— | 1 |
| Example 29 | 3,3-($CH_3$—)$_2$ | S | H | 4-$C_6H_5$—$C_6H_4$— | 1 |
| Example 30 | 3,3-($CH_3$—)$_2$ | S | H | 4-(4-F—$C_6H_5$)O—$C_6H_4$— | 1 |
| Example 31 | 3,3-($CH_3$—)$_2$ | S | H | 4-(4-Cl—$C_6H_5$)O—$C_6H_4$— | 1 |
| Example 32 | 3,3-($CH_3$—)$_2$ | S | H | 4-(4-Br—$C_6H_5$)O—$C_6H_4$— | 1 |
| Example 33 | 3,3-($CH_3$—)$_2$ | S | H | 4-(4-$Me_2$N—$C_6H_4$)O—$C_6H_4$— | 1 |
| Example 34 | 3,3-($CH_3$—)$_2$ | S | H | 4-(4-CN—$C_6H_4$)O—$C_6H_4$— | 1 |
| Example 35 | 3,3-($CH_3$—)$_2$ | S | H | 4-(4-MeO—$C_6H_4$)O—$C_6H_4$— | 1 |
| Example 36 | 3,3-($CH_3$—)$_2$ | S | H | 4-(4-$C_5H_4$N)O—$C_6H_4$— | 1 |
| Example 37 | 3,3-($CH_3$—)$_2$ | S | H | 4-(3-$C_5H_4$N)O—$C_6H_4$— | 1 |
| Example 38 | 3,3-($CH_3$—)$_2$ | S | H | 4-(2-$C_5H_4$N)O—$C_6H_4$— | 1 |
| Example 39 | 3,3-($CH_3$—)$_2$ | S | H | $C_6H_5CH_2CH_2$— | 1 |
| Example 40 | 3,3-($CH_3$—)$_2$ | S | H | $C_6H_5CH_2$— | 1 |
| Example 41 | 3,3-($CH_3$—)$_2$ | S | H | (4-$C_5H_4$N)$CH_2CH_2$— | 1 |
| Example 42 | 3,3-($CH_3$—)$_2$ | S | H | (2-$C_5H_4$N)$CH_2CH_2$— | 1 |
| Example 43 | 3,3-($CH_3$—)$_2$ | S | H | 4-($C_6H_{11}$)O—$C_6H_4$— | 1 |
| Example 44 | 3,3-($CH_3$—)$_2$ | S | H | 4-($C_5H_{11}$)O—$C_6H_4$— | 1 |
| Example 45 | 3,3-($CH_3$—)$_2$ | S | H | 4-($C_6H_{13}$)O—$C_6H_4$— | 1 |
| Example 46 | 3,3-($CH_3$—)$_2$ | S | H | 4-($CH_3OCH_2CH_2$)O—$C_6H_4$— | 1 |
| Example 47 | 3,3-($CH_3$—)$_2$ | S | H | 5-(2-pyridinyl)-2-thienyl- | 1 |
| Example 48 | 3,3-($CH_3$—)$_2$ | S | H | 5-(3-isoxazolyl)-2-thienyl- | 1 |
| Example 49 | 3,3-($CH_3$—)$_2$ | S | H | 5-(2-(methylthio)pyrimidin-4-yl)-2-thienyl- | 1 |
| Example 50 | 3,3-($CH_3$—)$_2$ | S | H | 5-(3-(1-methyl-5-(trifluoromethyl)pyrazolyl)-2-thienyl- | 1 |
| Example 51 | 3,3-($CH_3$—)$_2$ | $SO_2$ | H | 4-$NO_2$—$C_6H_4$— | 1 |
| Example 52 | 3,3-($CH_3$—)$_2$ | $SO_2$ | H | 4-i-BuO—$C_6H_4$— | 1 |
| Example 53 | 3,3-($CH_3$—)$_2$ | $SO_2$ | H | 4-($C_6H_5$)O—$C_6H_4$— | 1 |
| Example 54 | 3,3-($CH_3$—)$_2$ | $SO_2$ | H | 4-(4-F—$C_6H_4$)O—$C_6H_4$— | 1 |
| Example 55 | 3,3-($CH_3$—)$_2$ | $SO_2$ | H | 4-(4-Cl—$C_6H_4$)O—$C_6H_4$— | 1 |
| Example 56 | 3,3-($CH_3$—)$_2$ | $SO_2$ | H | 4-(4-Br—$C_6H_4$)O—$C_6H_4$— | 1 |
| Example 57 | 3,3-($CH_3$—)$_2$ | $SO_2$ | H | 4-(4-Me—$C_6H_4$)O—$C_6H_4$— | 1 |
| Example 58 | 3,3-($CH_3$—)$_2$ | $SO_2$ | H | 4-(4-MeO—$C_6H_4$)O—$C_6H_4$— | 1 |

-continued

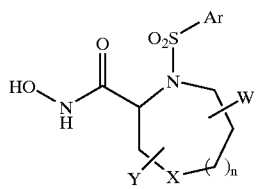

| | Y | X | W | Ar | n |
|---|---|---|---|---|---|
| Example 59 | 3,3-(CH$_3$—)$_2$ | SO$_2$ | H | 4-(4-CN—C$_6$H$_4$)O—C$_6$H$_4$— | 1 |
| Example 60 | 3,3-(CH$_3$—)$_2$ | SO$_2$ | H | 4-(4-Me$_2$N—C$_6$H$_4$)O—C$_6$H$_4$— | 1 |
| Example 61 | 3,3-(CH$_3$—)$_2$ | SO$_2$ | H | 4-EtO—C$_6$H$_4$— | 1 |
| Example 62 | 3,3-(CH$_3$—)$_2$ | SO$_2$ | H | 4-i-PrO—C$_6$H$_4$— | 1 |
| Example 63 | 3,3-(CH$_3$—)$_2$ | SO$_2$ | H | 4-n-PrO—C$_6$H$_4$— | 1 |
| Example 64 | 3,3-(CH$_3$—)$_2$ | SO$_2$ | H | 2-CH$_3$-4-Br—C$_6$H$_3$— | 1 |
| Example 65 | 3,3-(CH$_3$—)$_2$ | SO$_2$ | H | 4-C$_6$H$_5$—C$_6$H$_4$— | 1 |
| Example 66 | 3,3-(CH$_3$—)$_2$ | SO$_2$ | H | 4-(4-F—C$_6$H$_5$)—C$_6$H$_4$— | 1 |
| Example 67 | 3,3-(CH$_3$—)$_2$ | SO$_2$ | H | 4-(4-Cl—C$_6$H$_5$)—C$_6$H$_4$— | 1 |
| Example 68 | 3,3-(CH$_3$—)$_2$ | SO$_2$ | H | 4-(4-Br—C$_6$H$_5$)—C$_6$H$_4$— | 1 |
| Example 69 | 3,3-(CH$_3$—)$_2$ | SO$_2$ | H | 4-(4-Me$_2$N—C$_6$H$_4$)—C$_6$H$_4$— | 1 |
| Example 70 | 3,3-(CH$_3$—)$_2$ | SO$_2$ | H | 4-(4-CN—C$_6$H$_4$)—C$_6$H$_4$— | 1 |
| Example 71 | 3,3-(CH$_3$—)$_2$ | SO$_2$ | H | 4-(4-MeO—C$_6$H$_4$)—C$_6$H$_4$— | 1 |
| Example 72 | 3,3-(CH$_3$—)$_2$ | SO$_2$ | H | 4-(4-C$_5$H$_4$N)O—C$_6$H$_4$— | 1 |
| Example 73 | 3,3-(CH$_3$—)$_2$ | SO$_2$ | H | 4-(3-C$_5$H$_4$N)O—C$_6$H$_4$— | 1 |
| Example 74 | 3,3-(CH$_3$—)$_2$ | SO$_2$ | H | 4-(2-C$_5$H$_4$N)O—C$_6$H$_4$— | 1 |
| Example 75 | 3,3-(CH$_3$—)$_2$ | SO$_2$ | H | C$_6$H$_5$CH$_2$CH$_2$— | 1 |
| Example 76 | 3,3-(CH$_3$—)$_2$ | SO$_2$ | H | C$_6$H$_5$CH$_2$— | 1 |
| Example 77 | 3,3-(CH$_3$—)$_2$ | SO$_2$ | H | (4-C$_5$H$_4$N)CH$_2$CH$_2$— | 1 |
| Example 78 | 3,3-(CH$_3$—)$_2$ | SO$_2$ | H | (2-C$_5$H$_4$N)CH$_2$CH$_2$— | 1 |
| Example 79 | 3,3-(CH$_3$—)$_2$ | SO$_2$ | H | C$_6$H$_5$CH$_2$CH$_2$— | 1 |
| Example 80 | 3,3-(CH$_3$—)$_2$ | SO$_2$ | H | C$_6$H$_5$CH$_2$— | 1 |
| Example 81 | 3,3-(CH$_3$—)$_2$ | SO$_2$ | H | (4-C$_5$H$_4$N)CH$_2$CH$_2$— | 1 |
| Example 82 | 3,3-(CH$_3$—)$_2$ | SO$_2$ | H | (2-C$_5$H$_4$N)CH$_2$CH$_2$— | 1 |
| Example 83 | 3,3-(CH$_3$—)$_2$ | SO$_2$ | H | 4-(C$_6$H$_{11}$)O—C$_6$H$_4$— | 1 |
| Example 84 | 3,3-(CH$_3$—)$_2$ | SO$_2$ | H | 4-(C$_5$H$_{11}$)O—C$_6$H$_4$— | 1 |
| Example 85 | 3,3-(CH$_3$—)$_2$ | SO$_2$ | H | 4-(C$_6$H$_{13}$)O—C$_6$H$_4$— | 1 |
| Example 86 | 3,3-(CH$_3$—)$_2$ | SO$_2$ | H | 4-(CH$_3$OCH$_2$CH$_2$)O—C$_6$H$_4$— | 1 |
| Example 87 | 3,3-(CH$_3$—)$_2$ | SO$_2$ | H | 5-(2-pyridinyl)-2-thienyl- | 1 |
| Example 88 | 3,3-(CH$_3$—)$_2$ | SO$_2$ | H | 5-(3-isoxazolyl)-2-thienyl- | 1 |
| Example 89 | 3,3-(CH$_3$—)$_2$ | SO$_2$ | H | 5-(2-(methylthio)pyrimidin-4-yl)-2-thienyl- | 1 |
| Example 90 | 3,3-(CH$_3$—)$_2$ | SO$_2$ | H | 5-(3-(1-methyl-5-(trifluoromethyl)pyrazolyl)-2-thienyl- | 1 |
| Example 91 | 3,3-(CH$_3$—)$_2$ | CH$_2$ | H | 4-(C$_6$H$_5$)O—C$_6$H$_4$— | 1 |
| Example 92 | 3,3-(CH$_3$—)$_2$ | CH$_2$ | H | 4-(4-F—C$_6$H$_4$)O—C$_6$H$_4$— | 1 |
| Example 93 | 3,3-(CH$_3$—)$_2$ | CH$_2$ | H | 4-(4-Cl—C$_6$H$_4$)O—C$_6$H$_4$— | 1 |
| Example 94 | 3,3-(CH$_3$—)$_2$ | CH$_2$ | H | 4-(4-Br—C$_6$H$_4$)O—C$_6$H$_4$— | 1 |
| Example 95 | 3,3-(CH$_3$—)$_2$ | CH$_2$ | H | 4-(4-Me—C$_6$H$_4$)O—C$_6$H$_4$— | 1 |
| Example 96 | 3,3-(CH$_3$—)$_2$ | CH$_2$ | H | 4-(4-MeO—C$_6$H$_4$)O—C$_6$H$_4$— | 1 |
| Example 97 | 3,3-(CH$_3$—)$_2$ | CH$_2$ | H | 4-(4-CN—C$_6$H$_4$)O—C$_6$H$_4$— | 1 |
| Example 98 | 3,3-(CH$_3$—)$_2$ | CH$_2$ | H | 4-(4-Me$_2$N—C$_6$H$_4$)O—C$_6$H$_4$— | 1 |
| Example 99 | 3,3-(CH$_3$—)$_2$ | CH$_2$ | H | 4-(4-C$_5$H$_4$N)O—C$_6$H$_4$— | 1 |
| Example 100 | 3,3-(CH$_3$—)$_2$ | CH$_2$ | H | 4-(3-C$_5$H$_4$N)O—C$_6$H$_4$— | 1 |
| Example 101 | 3,3-(CH$_3$—)$_2$ | CH$_2$ | H | 4-(2-C$_5$H$_4$N)O—C$_6$H$_4$— | 1 |

Methods

Examples 15–50 are prepared analogously to Example 1 using the appropriately functionalized sulfonyl chloride. The sulfonyl chlorides which are used to prepare the above examples are either purchased from commercial sources or prepared via known methods. For example, the 4-phenoxyphenylsulfonyl chloride used for the preparation of Example 17, was prepared as described by R. J. Cremlyn et al in *Aust. J. Chem.*, 1979, 32, 445.52.

Examples 51–90 are prepared by oxidation of the corresponding sulfide (found in Examples 15–50). The oxidation proceeds in a manner analogous to Example 2.

Examples 91–101 are prepared analogously to Example 13 using the appropriately functionalized sulfonyl chloride.

These examples provide the skilled artisan with sufficient guidance as to making the present invention and do not limit it in any way.

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case the compounds formula I may be substituted for the example compound shown below with similar results.

The methods of use exemplified do not limit the invention, but provide guidance to the skilled artisan to use the compounds, compositions and methods of the invention. The skilled practitioner will appreciate that the examples provide guidance and may be varied based on condition and the patient.

Example A

A tablet composition for oral administration, according to the present invention, is made comprising:

| Component | Amount |
|---|---|
| Example 2a | 15. mg |
| Lactose | 120. mg |
| Maize Starch | 70. mg |
| Talc | 4. mg |
| Magnesium Stearate | 1. mg |

Other compounds having a structure according to Formula (I) are used with substantially similar results.

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| Example 1 | 15% |
| Polyethylene glycol | 85% |

Other compounds having a structure according to Formula (I) are used with substantially similar results.

A human male subject weighing 90 kg (198 lbs), suffering from osteoarthritis, is treated by a method of this invention. Specifically, for 5 years, a capsule containing 70 mg of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component | Amount (% w/w) |
|---|---|
| Example 1 | 5% |
| Polyvinyl alcohol | 15% |
| Saline | 80% |

Other compounds having a structure according to Formula (I) are used with substantially similar results.

A patient having deep corneal abrasion applies the drop to each eye twice a day. Healing is speeded, with no visual sequelae.

Example D

An topical composition for local administration, according to the present invention, is made comprising:

| Component | Composition (% w/v) |
|---|---|
| Compound of Example 2b. | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |
| Total = | 100.00 |

Any of the other compounds having a structure according to Formula (I) are used with substantially similar results.

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 2c. | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Any of the other compounds having a structure according to Formula (I) are used with substantially similar results.

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 1 | 0.10 |
| Benzalkonium chloride | 0.01 |
| EDTA | 0.05 |
| Hydroxyethylcellulose (NATROSOL M ™) | 0.50 |
| Sodium metabisulfite | 0.10 |
| Sodium chloride (0.9%) | q.s. |
| Total = | 100.0 |

Any of the other compounds having a structure according to Formula (I) are used with substantially similar results.

A human male subject weighing 90 kg (198 lbs), suffering from corneal ulcerations, is treated by a method of this invention. Specifically, for 2 months, a saline solution containing 10 mg of Example 5 is administered to said subject's affected eye twice-daily.

Example G

A composition for parenteral administration is made comprising:

| Component | Amount |
|---|---|
| Example 2b. | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Other compounds having a structure according to Formula I are used with substantially similar results.

Example H

A mouthwash composition is prepared,

| Component | % w/v |
|---|---|
| Example 2c. | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 ml of the mouthwash thrice daily to prevent further oral degeneration.

Other compounds having a structure according to Formula I are used with substantially similar results.

Example I

A lozenge composition is prepared;

| Component | % w/v |
|---|---|
| Example 2a. | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the losenge to prevent loosening of an implant in the maxilla. Other compounds having a structure according to Formula I are used with substantially similar results.

Example J

Chewing Gum Composition

| Component | w/v % |
|---|---|
| Example 1 | 0.03 |
| Sorbitol crystals | 38.44 |
| Paloja-T gum base* | 20.00 |
| Sorbitol (70% aqueous solution) | 22.00 |
| Mannitol | 10.00 |
| Glycerine | 7.56 |
| Flavor | 1.00 |

A patient chews the gum to prevent loosening to prevent loosening of dentures.

Other compounds having a structure according to Formula I are used with substantially similar results.

Example K

| Components | w/v % |
|---|---|
| USP Water | 54.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

Example 1 is prepared by first mixing 80 kg of gylcerin and all of the benzyl alcohol and heating to 65 C, then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes.

The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

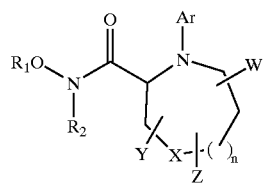

wherein

R$_1$ is H;

R$_2$ is hydrogen, alkyl or acyl;

Ar is COR$_3$ or SO$_2$R$_4$; and

R$_3$ is selected from the group consisting of alkoxy, aryloxy, heteroaryloxy, alkyl, aryl, heteroaryl, heteroalkyl, amino, alkylamino, dialkylamino, arylamino and alkylarylamino;

R$_4$ is aryl, substituted or unsubstituted;

X is selected from the group of O, S, SO and SO$_2$;

R$_6$ is selected from the group consisting of alkyl, aryl, heteroaryl, heteroalkyl, amino, alkylamino, dialkylamino, arylamino, diarylamino and alkylarylamino:

R$_7$ is selected from the group consisting of hydrogen, alkoxy, aryloxy, heteroaryloxy, alkyl, aryl, heteroaryl, heteroalkyl, amino, alkylamino, dialkylamino, arylamino and alkylarylamino;

R$_8$ is selected from the group consisting of alkyl, aryl, heteroaryl, heteroalkyl, amino, alkylamino, dialkylamino, arylamino, diarylamino and alkylarylamino;

R$_9$ is selected from the group consisting of alkyl, aryl, heteroaryl and heteroalkyl;

W is hydrogen or one or more lower alkyl moieties;

Y is selected from the group consisting of independently one or more of hydrogen, hydroxy, SR$_{10}$, SOR$_4$, SO$_2$R$_4$, alkoxy and amino, wherein amino is of formula NR$_{11}$R$_{12}$, wherein R$_{11}$ and R$_{12}$ are independently chosen from hydrogen, alkyl, heteroalkyl, heteroaryl, aryl, SO$_2$R$_6$, COR$_7$, CSR$_8$ and PO(R$_9$)$_2$; and R$_{10}$ is selected from the group consisting of hydrogen, alkyl, aryl and heteroaryl;

Z is nil, a spiro moiety or an oxo group substituted on the heterocyclic ring;

n is 3;

or an optical isomer, diastereomer or enantiomer of Formula (I), or a pharmaceutically-acceptable salt thereof.

2. The compound of claim 1, wherein X is selected from the group consisting of O, S, SO and SO$_2$.

3. The compound of claim 1, wherein Ar is SO$_2$R$_4$.

4. The compound of claim 1, wherein R$_4$ is phenyl or substituted phenyl.

5. The compound of claim 4, wherein R$_4$ is substituted phenyl and the substitution is with hydroxy, alkoxy, nitro or halo.

6. The compound of claim 5, wherein R$_4$ is substituted with methoxy, bromo, nitro and butoxy.

7. The compound of claim 6, wherein R$_4$ is substituted at the ortho or para position relative to the sulfonyl.

8. The compound if claim 1, wherein W is one more of hydrogen or C$_1$ to C$_4$ alkyl.

9. The compound of claim 1, wherein W is geminal and each geminal substitution can be from C$_1$ to C$_4$ alkyl.

10. The compound of claim 1 wherein Z is an oxo moiety substituted on the heterocyclic ring.

11. A pharmaceutical composition comprising:
   (a) a safe and effective amount of a compound of claim 1; and
   (b) a pharmaceutically-acceptable carrier.

12. A pharmaceutical composition comprising:
   (a) a safe and effective amount of a compound of claim 4; and
   (b) a pharmaceutically-acceptable carrier.

13. A pharmaceutical composition comprising:
   (a) a safe and effective amount of a compound of claim 5; and
   (b) a pharmaceutically-acceptable carrier.

14. A pharmaceutical composition comprising:
   (a) a safe and effective amount of a compound of claim 9; and
   (b) a pharmaceutically-acceptable carrier.

15. A pharmaceutical composition comprising:
   (a) a safe and effective amount of a compound of claim 10; and
   (b) a pharmaceutically-acceptable carrier.

* * * * *

UNITED STATES PATENT AND TRADEMARK OFFICE
CERTIFICATE OF CORRECTION

PATENT NO. : 6,545,038 B1
DATED : April 8, 2003
INVENTOR(S) : Biswanath De

It is certified that error appears in the above-identified patent and that said Letters Patent is hereby corrected as shown below:

Column 36,
Line 18, delete "MeO" and insert -- OH --.
Line 66, delete "5" in "2(5)N" and insert -- S -- to read -- 2(S)N --.

Column 37,
Line 27, delete "butyldimethylsilyl-propyl" and insert -- butyldimethylsiloxy-propyl --.
Line 58, delete "methozymethyl" and insert -- methoxymethyl --.

Column 38,
Lines 12, 13 and 17, delete "wa" and insert -- was --.
Line 52, delete "oxo" and insert -- dioxo --.

Column 39,
Line 28, delete "H⁻" and insert -- H⁺ --.
Line 36, insert a -- - -- after the first closed parenthesis and before the "N".

Column 40,
Line 26, insert a -- - -- between the "S" and open parenthesis before the number "2".

Column 41,
Line 15, insert a -- - -- between the number "4" and the word "thiazonine".

Column 42,
Line 63, delete "2s" and insert -- 2S --.
Line 65, delete "saodium" and insert -- sodium --.

Column 43,
Line 10, delete "thiolidne" and insert -- thiazolidine --.
Line 39, insert a -- — -- between the "S" and the open parenthesis before the number "2".

Column 46,
Line 12, delete "cycloexanecarboxylate" and insert -- cyclohexanecarboxylate --.

Column 47,
Line 14, delete "dimethyhexahydro" and insert -- dimethyl-hexahydro --.
Line 36, insert a -- - -- between the number "1" and the open bracket "[".

UNITED STATES PATENT AND TRADEMARK OFFICE
CERTIFICATE OF CORRECTION

PATENT NO. : 6,545,038 B1
DATED : April 8, 2003
INVENTOR(S) : Biswanath De

It is certified that error appears in the above-identified patent and that said Letters Patent is hereby corrected as shown below:

<u>Column 50,</u>
Examples 34 and 35, delete "O" after the closed parenthesis.

<u>Column 56,</u>
Line 17, delete the duplicated "to prevent loosening".

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,545,038 B1
DATED : April 8, 2003
INVENTOR(S) : Biswanath De

It is certified that error appears in the above-identified patent and that said Letters Patent is hereby corrected as shown below:

<u>Column 3,</u>
Lines 11-13, please delete "Ar is substituted phenyl, the substituents are hydroxy, alkoxy, nitro or halo and preferably the substituents are methoxy, bromo, nitro and butoxy."

Signed and Sealed this

Tenth Day of August, 2004

JON W. DUDAS
*Acting Director of the United States Patent and Trademark Office*